United States Patent [19]
Schwartz et al.

[11] Patent Number: 5,821,072
[45] Date of Patent: Oct. 13, 1998

[54] COMBINATIONS OF PKC INHIBITORS AND THERAPAEUTIC AGENTS FOR TREATING CANCERS

[75] Inventors: Gary K. Schwartz, Briarcliff Manor; Anthony P. Albino, New York, both of N.Y.

[73] Assignee: Sloan-Kettering Institute for Cancer Research, New York, N.Y.

[21] Appl. No.: 603,814

[22] Filed: Feb. 20, 1996

[51] Int. Cl.$^6$ .............................. C12Q 1/48; C12N 9/10
[52] U.S. Cl. ..................... 435/15; 435/193; 435/194; 435/7.1; 435/7.23; 424/9.2
[58] Field of Search ...................... 435/194, 15, 7.23, 435/32, 193; 514/1; 424/9.2

[56] References Cited

PUBLICATIONS

Ponnathpur, et al., (1995) "Effects of Modulators of Protein Kinases on Taxol–induced Apoptosis of Human Leukemic Cells Possessing Disparate Levels of p26BCL–2 Protein", Clinical Cancer Research, vol. 1: 1399–1406.

Schwartz, et al., (1991) "Protein Kinase C Activity and Multidrug Resistance in MOLT–3 Human Lymphoblastic Leukemia Cells Resistant to Timetrexate", Cancer Research, vol. 51: 55–61.

Schwartz, et al., (1995) "Potentiation of Apoptosis by Treatment with Protein Kinase C–Specific Inhibitor Safingol in Mitomycin C–Treated Gastric Cancer Cells", Journal of the National Cancer Institute, vol. 87: 1394–1399.

Wang, et al., (1995) "Apoptosis in 7–Hydroxystauropurine–treated T Lymphoblasts Correlates with Activation of Cyclin–dependent Kinases 1 and 2", Cell Growth and Differentiation, vol. 6: 927–936.

Jarvis, D., et al. (1994) "Effects of Bryostatin 1 and other Pharmacological Activators Of Protein Kinase C on 1–[β–D–Arabinofuranosyl] Cytosine–induced Apoptosis in HL–60 Human Promyelocytic Leukemia Cells", Biochemical Pharmacology, vol. 47, No. 5: 839–852.

Mohammad, R. et al., (1994) "Successful Treatment of Human Waldenstrom's Macroglobulinemia with Combination Biological and Chemotherapy Agents", Cancer Research, vol. 54: 165–168.

Mohammad, R. et al., (1995) "Bryostatin 1 induces Apoptosis and augments Inhibitory effects of Vincristine in Human Diffuse Large Cell Lymphoma", Leukemia Research, vol. 19, No. 9:667–673.

Foti, et al., (1995) "Proceedings of the American Association for Cancer Research", American Association for Cancer Research, vol. 36: 11.

Haimovitz–Friedman, et al., (1994) "Protein Kinase C Mediates Basic Fibroblast Growth Factor Protection of Endothelial Cells against Radiation–induced Apoptosis", Cancer Research, vol. 54: 2591–1597.

Akinaga, et al., (1993) "Enhancement of antitumor activity of mitomycin C in vitro and in vivo by UCN–01, a selective inhibitor of protein kinase C", Cancer Chemother.Pharmacol., vol. 32: 183–189.

Foti, et al., (1993) "Proceedings of the American Association for Cancer Research", American Association for Cancer Research, vol. 34: 410–411.

Lane (1993), Nature 362: 786–787. "A death in the life of p. 53".

*Primary Examiner*—Robert A. Wax
*Assistant Examiner*—Nashaat T. Nashed
*Attorney, Agent, or Firm*—John P. White; Cooper & Dunham LLP

[57] ABSTRACT

This invention provides methods for screening protein kinase C inhibitors capable of potentiating apoptosis in tumor cells. This invention also provides methods for screening antitumor therapeutic agents suitable for combination therapy with a protein kinase C inhibitors capable of potentiating apoptosis in tumor cells. This invention further provides different combination therapies comprising the specific protein kinase C inhibitors and the antitumor therapeutic agents.

3 Claims, 10 Drawing Sheets

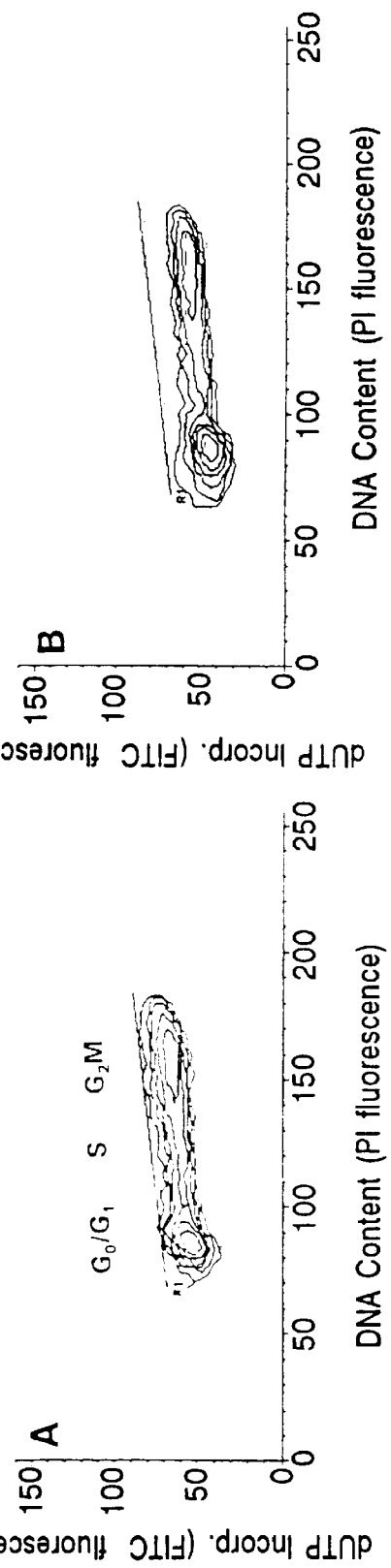
FIG. 3A
FIG. 3B
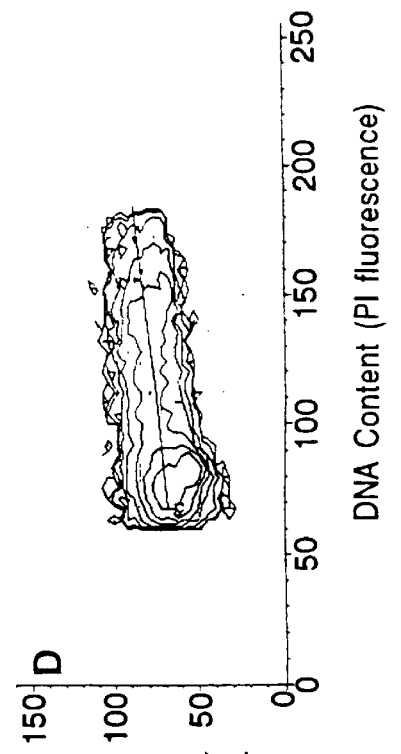
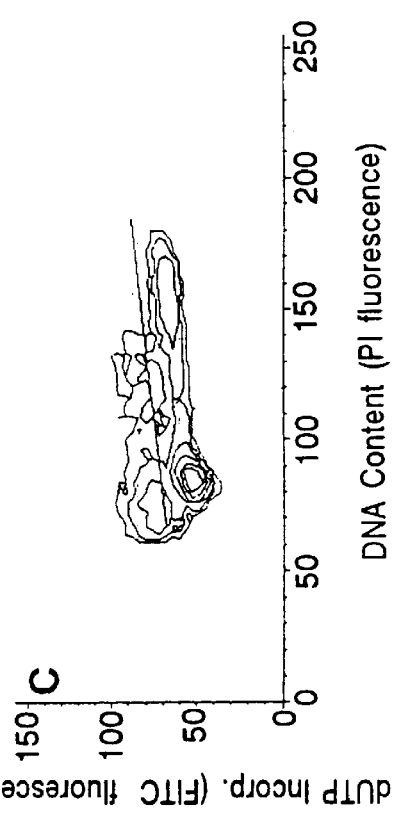
FIG. 3C
FIG. 3D

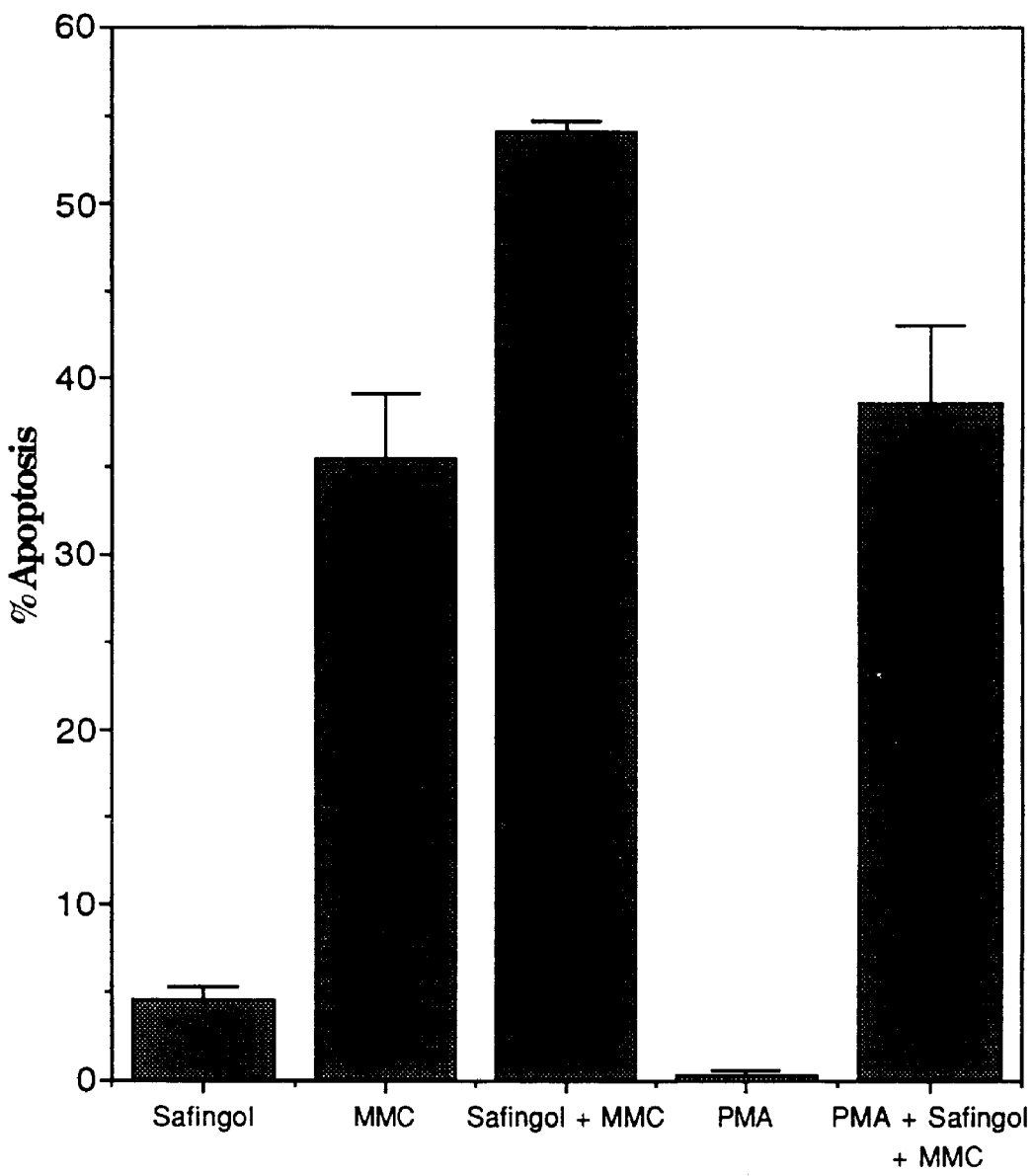

5,821,072

COMBINATIONS OF PKC INHIBITORS AND THERAPAEUTIC AGENTS FOR TREATING CANCERS

BACKGROUND OF THE INVENTION

Throughout this application, various references are referred to within parentheses. Disclosures of these publications in their entireties are hereby incorporated by reference into this application to more fully describe the state of the art to which this invention pertains. Full bibliographic citation for these references may be found at the end of each series of experiments in this application, preceding the claims.

Protein kinase C (PKC) functions in processes relevant to carcinogenesis, tumor cell metastasis, and apoptosis. Safingol, an optical isomer (the L-threo enantiomer) of dihydrosphingosine, is a specific inhibitor of PKC and may represent a novel target for anti-cancer therapy. Preclinical animal studies show that safingol alone has minimal effects on tumor cell growth, but combination of this compound with conventional chemotherapy agents dramatically potentiates their anti-tumor effects. It has been suggested that many chemotherapeutic agents exert their anti-tumor effects by inducing apoptosis.

A large body of evidence indicates a fundamental role for the involvement of protein kinase C (PKC), family members of serine/threonine protein kinases, in processes relevant to neoplastic transformation, carcinogenesis, and tumor cell invasion of surrounding tissues (1–3). Consequently, PKC may represent a novel target for anti-cancer therapy. Safingol, the L-threo enantiomer of dihydrosphingosine, is a specific inhibitor of PKC (4). Preclinical animal studies show that safingol is non-toxic at doses that achieve serum levels sufficient to inhibit PKC enzyme activity (5). While safingol has negligible impact on tumor cell growth in vivo, the combination of safingol with conventional chemotherapeutic agents such as doxorubicin and cisplatin significantly potentiates the anti-tumor effects of these drugs (6).

Based on these observations, safingol, used in combination with doxorubicin, has become the first PKC specific inhibitor to enter clinical trials. The mechanism by which safingol potentiates the activity of chemotherapeutic agents is unclear, although inhibition of P-glycoprotein phosphorylation and reversal of the multidrug resistant (mdr) phenotype have been suggested (7,8). While this hypothesis can explain the synergism achieved with combinations of safingol and doxorubicin, it does not explain the synergism reported for combinations of safingol with drugs that are not believed to produce resistance by the mdr mechanism (e.g., cisplatin) (6), nor does it explain safingol-induced effects that occur in tumor cell lines that do not express the P-glycoprotein (8). Therefore, pathways other than P-glycoprotein inhibition are likely to be involved in the safingol-mediated enhancement of chemotherapy.

It has been suggested that the anti-tumor activity of many chemotherapeutic agents (e.g., cisplatin and etoposide) is a consequence of their induction of apoptosis (9). In this context it has been proposed that activation of PKC acts as an antagonist to apoptosis, whereas inhibition of PKC promotes apoptosis (10–12). Thus, safingol-mediated potentiation of chemotherapy might be attributed to its PKC inhibitory effect, subsequently leading to increased apoptosis after drug-induced damage.

The present studies sought to determine the extent to which whether safingol by itself, or in combination with a specific chemotherapeutic drug (e.g. mitomycin-C, MMC), would promote apoptosis in gastric cancer cells. Furthermore, applicants investigated whether the p53 status of these cells influences the development of apoptosis after treatment with safingol and MMC.

SUMMARY OF THE INVENTION

This invention provides a method for screening protein kinase C inhibitors capable of potentiating apoptosis in tumor cells comprising steps of (a) contacting an amount of a protein kinase C inhibitors with tumor cells effective to potentiate apoptosis of tumor cells; (b) contacting the potentiated tumor cells of step (a) with an antitumor therapeutic agent; (c) determining the apoptosis of tumor cells; and (d) comparing the apoptosis determined in step (c) with apoptosis of same tumor cells which are only treated with the antitumor therapeutic agent, an increase in apoptosis indicating that the protein kinase C inhibitor is capable of potentiating apoptosis in tumor cells. This invention also provide the above method, wherein step (a) is carried out in the presence of the antitumor therapeutic agent.

This invention also provides the protein kinase C inhibitor capable of potentiating apoptosis in tumor cells as determined by the above-described methods.

This invention further provides a pharmaceutical composition comprising the protein kinase C inhibitor capable of potentiating apoptosis in tumor cells as determined by the above-described methods and a pharmaceutically acceptable carrier.

This invention provides a method for screening antitumor therapeutic agents suitable for combination therapy with a protein kinase C inhibitors capable of potentiating apoptosis in tumor cells comprising steps of: (a) contacting an amount of a protein kinase C inhibitor with tumor cells effective to potentiate apoptosis of tumor cells; (b) contacting the potentiated tumor cells of step (a) with an antitumor therapeutic agent; (c) determining the apoptosis of tumor cells; and (d) comparing the apoptosis determined in step (c) with apoptosis of same tumor cells which are only treated with the protein kinase C inhibitor, an increase in apoptosis indicating that the antitumor therapeutic agent is suitable for combination therapy with a protein kinase C inhibitor capable of potentiating apoptosis in tumor cells. In an embodiment, step (a) is carried out in the presence of the protein kinase C inhibitor. In another embodiment, the antitumor therapeutic agent is not previously known.

This invention also provides an antitumor therapeutic agent suitable for combination therapy with a protein kinase C inhibitors capable of potentiating apoptosis in tumor cells determined by the above-described methods.

This invention also provides a pharmaceutical composition comprising an effective amount of the antitumor therapeutic agent determined by the above-described methods, a protein kinase C inhibitor capable of potentiating apoptosis in tumor cells and a pharmaceutically acceptable carrier.

This invention provides a method for enhancing therapy in a tumor bearing subject comprising administering to the subject an effective amount of a specific protein kinase C inhibitor capable of potentiating apoptosis in tumor cells during or prior to the treatment of an antitumor therapeutic agent. This invention provides the above method, wherein the specific protein kinase C inhibitor is Safingol (L-threo-dihydrosphingosine), RO32-0432 (Bisindolylmaleimide tertiary amine), UCN-01 (7-OH-staurosporine), Flavopiridol (L86-8275), Bryostatin 1 (Macrocyclic lactone) or antisense nucleotides capable of inhibiting the expression of the protein kinase C.

In an embodiment, the antitumor therapeutic agent is a chemotherapeutic agent. In a further embodiment, the chemotherapeutic agent is selected from a group consisting of Mitomycin C, Carboplatin, Taxol and Doxorubicin. In a still further embodiment, the antitumor therapeutic agent is a radiotherapeutic agent In an embodiment of the above-described methods, the tumor is a gastrointestinal cancer. In a further embodiment, the gastrointestinal cancer is gastric cancer, small bowel cancer, colon cancer or rectal cancer.

In a separate embodiment of the above-described methods, the tumor is a breast cancer. In another embodiment, the tumor is a ovarian cancer. In a still another embodiment, the tumor is of prostate cancer, lung cancer, melanoma, cervical carcinoma, pancreatic cancer, sarcoma, hepatoma, gallbladder cancer, leukemia or lymphoma.

Finally, this invention provides a method for potentiating apoptosis in tumor cells comprising contacting the cancerous cells with an effective amount of a specific protein kinase C inhibitor capable of potentiating apoptosis during or prior to the treatment of an antitumor therapeutic agent.

BRIEF DESCRIPTION OF THE FIGURES

FIG. 3. Contour plots are shown for the frequency of MKN-74 cells exhibiting increased green fluorescence emitted from digoxigenin-dUTP:fluorescein isothyiocyanate-labeled antibody complexes [dUTP Incorp. (FITC fluorescence)], which identifies subpopulations of cells undergoing apoptosis by the TdT assay, versus cellular DNA content (PI fluorescence), as described in the "Material and Methods" section. MKN-74 cells were incubated for 24 hours with no drug (panel A), safingol alone (50 $\mu$M, panel B), MMC alone (5 $\mu$g/ml, panel C), or the combination of safingol (50 $\mu$M) and MMC (5 $\mu$g/ml) (panel D). Apoptotic cells are identified as those sorting above the $R_1$ region of the contour plots. The $G_0/G_1$, S, and $G_2$/M regions of the cell cycle are indicated in Panel A.

FIG. 4. Effect of PKC activation with PMA on the induction of apoptosis in the presence of the PKC inhibitor safingol. SK-GT-5 cells were treated, as described in "Materials and Methods," according to the following protocols: safingol alone (50 $\mu$M) for 1 hour followed by no drug for 24 hours; MMC alone (5 $\mu$g/ml) for 24 hours; safingol alone (50 $\mu$M) for 1 hour followed MMC (5 $\mu$g/ml) alone for 24 hours; PMA alone (1 ng/ml) for 1 hour, followed by no drug for 24 hours; and the combination of safingol (50 $\mu$M) and PMA (1 ng/ml) for 1 hour, followed by MMC alone (5 $\mu$g/ml) for 24 hours. Induction of apoptosis was then determined with the QFM staining of condensed nuclear chromatin. Bars represent mean number of cells counted that undergo apoptosis as a percentage of 500 total cells randomly counted in duplicate samples, ±SD.

Applicants' studies indicate that flavopiridol increased the induction of apoptosis from 7%±1% with MMC alone to 73%±1% with MMC and flavopiridol in combination. Flavopiridol alone induced a slight degree of apoptosis (17%±2%), but not nearly to the degree observed with the combination therapy.

Figure 8:
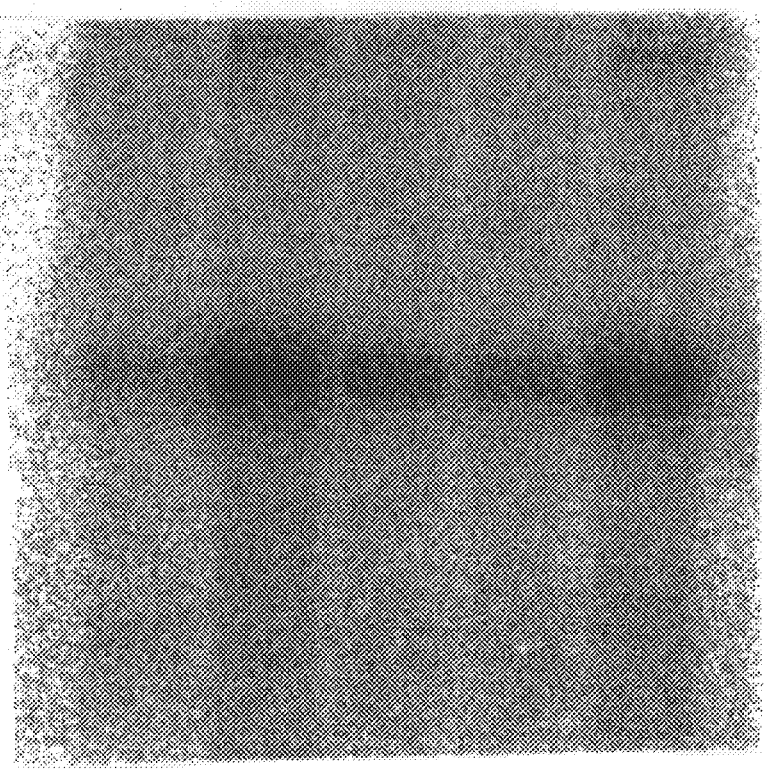

FIG. 8. Each lane represents the following: lane A, the IgG control; lane B, no drug therapy for 24 hours; lane C, MMC alone (5.0 $\mu$g/ml) for 24 hours; lane D, safingol alone (50 $\mu$M) for 24 hours; lane E, the combination of safingol (50 $\mu$M) and MMC (5.0 $\mu$g/ml) for 24 hours. The results indicate that untreated gastric cancer cells (lane B) have increased cdk2 activity and that both MMC (lane C) and safingol (lane D) have decreased cdk2. However, the combination of MMC and safingol increased cdk2 activity back to basal levels.

Figure 9:
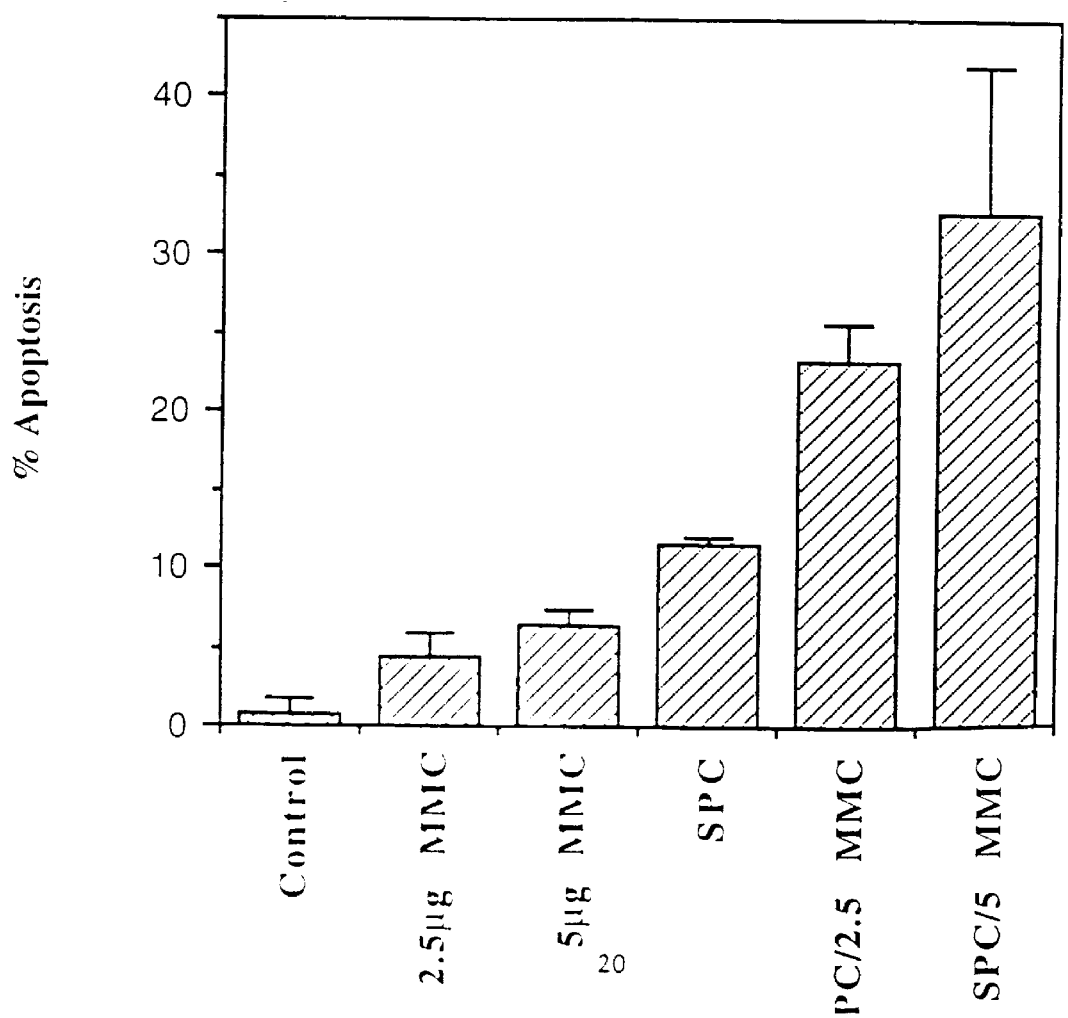

FIG. 9. MMC alone at the concentrations of 2.5 $\mu$g/ml and 5.0 $\mu$g/ml induced apoptosis in 4%±2 and 6%±1 of the MDA-MB-468 cells, respectively. However, the combination of safingol (SPC) and MMC significantly increased the percentage of cells undergoing apoptosis from 11%±1 with safingol alone to 23%±2 with safingol and 2.5 $\mu$g/ml MMC and to 33%±10 with safingol and 5.0 $\mu$g/ml MMC (p<0.001).

Figure 10:
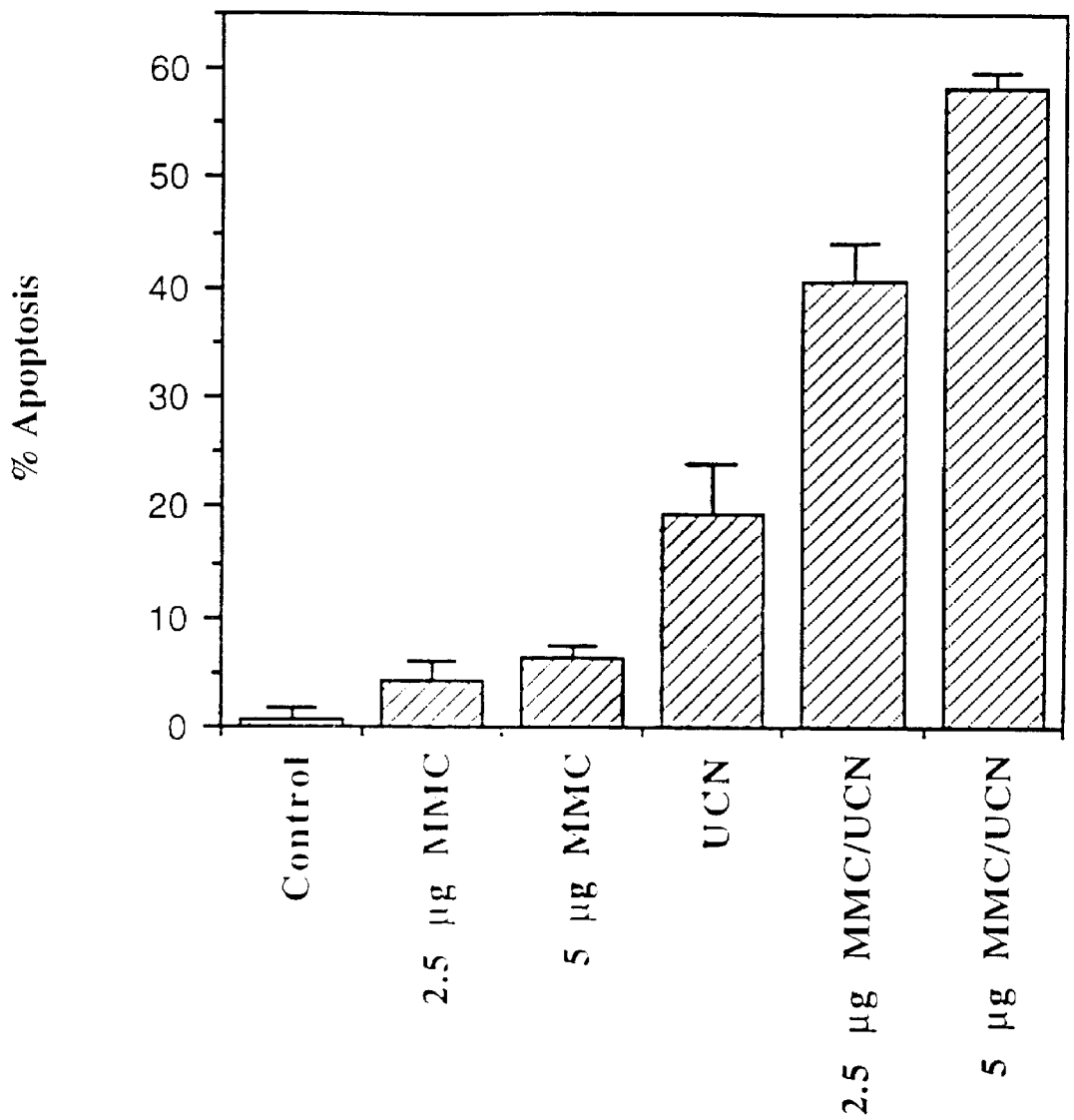

FIG. 10. The combination of UCN-01 and MMC together increased the induction of apoptosis of the MDA-MB-468 cells from 20%±4 with UCN-01 alone to 41%±3 with UCN-01 and 2.5 $\mu$g/ml MMC and to 58%±1 with UCN-01 and 5.0 $\mu$g/ml MMC.

DETAILED DESCRIPTION OF THE INVENTION

This invention provides a method for screening protein kinase C inhibitors capable of potentiating apoptosis in tumor cells comprising steps of (a) contacting an amount of a protein kinase C inhibitor with tumor cells effective to potentiate apoptosis of tumor cells; (b) contacting the potentiated tumor cells of step (a) with an antitumor therapeutic agent; (c) determining the apoptosis of tumor cells; and (d) comparing the apoptosis determined in step (c) with apoptosis of same tumor cells which are only treated with the antitumor therapeutic agent, an increase in apoptosis indicating that the protein kinase C inhibitor is capable of potentiating apoptosis in tumor cells.

This invention also provide the above method, wherein step (a) is carried out in the presence of the antitumor therapeutic agent. In an embodiment, the protein kinase C inhibitor is not previously known.

This invention also provides the protein kinase C inhibitor capable of potentiating apoptosis in tumor cells as determined by the above-described methods.

This invention further provides a pharmaceutical composition comprising the protein kinase C inhibitor capable of potentiating apoptosis in tumor cells as determined by the above-described methods and a pharmaceutically acceptable carrier.

This invention provides a method for screening antitumor therapeutic agents suitable for combination therapy with a protein kinase C inhibitors capable of potentiating apoptosis in tumor cells comprising steps of: (a) contacting an amount of a protein kinase C inhibitor with tumor cells effective to potentiate apoptosis of tumor cells; (b) contacting the potentiated tumor cells of step (a) with an antitumor therapeutic agent; (c) determining the apoptosis of tumor cells; and (d) comparing theaapoptosis determined in step (c) with apoptosis of same tumor cells which are only treated with the protein kinase C inhibitor, an increase in apoptosis indicating that the antitumor therapeutic agent is suitable for combination therapy with a protein kinase C inhibitor capable of potentiating apoptosis in tumor cells. In an embodiment, step (a) is carried out in the presence of the protein kinase C inhibitor. In another embodiment, the antitumor therapeutic agent is not previously known.

This invention also provides an antitumor therapeutic agent suitable for combination therapy with a protein kinase C inhibitors capable of potentiating apoptosis in tumor cells determined by the above-described methods.

This invention also provides a pharmaceutical composition comprising an effective amount of the antitumor therapeutic agent determined by the above-described methods, a protein kinase C inhibitor capable of potentiating apoptosis in tumor cells and a pharmaceutically acceptable carrier.

This invention provides a method for enhancing therapy in a tumor bearing subject comprising administering to the subject an effective amount of a specific protein kinase C inhibitor capable of potentiating apoptosis in tumor cells during or prior to the treatment of an antitumor therapeutic agent. This invention provides the above method, wherein the specific protein kinase C inhibitor is selected from a group consisting of Safingol (L-threo-dihydrosphingosine), RO32-0432 (Bisindolylmaleimide tertiary amine), UCN-01 (7-OH-staurosporine), Flavopiridol (L86-8275), Bryostatin 1 (Macrocyclic lactone) and antisense nucleotides capable of inhibiting the expression of the protein kinase C. The above specific protein kinase C inhibitors are simply described for illustrative purposes of this invention. As it will be appreciated by a person of ordinary skill in the art that other specific protein kinase inhibitors may be used in this invention. Applicants have provided as methodology to determine whether a protein kinase C inhibitor may be useful for the claimed combination therapy.

In an embodiment, the antitumor therapeutic agent is a chemotherapeutic agent. In a further embodiment, the chemotherapeutic agent is Mitomycin C, Carboplatin, Taxol or Doxorubicin. In a still further embodiment, the antitumor therapeutic agent is a radiotherapeutic agent In an embodiment of the above-described methods, the tumor is a gastrointestinal cancer. In a further embodiment, the gastrointestinal cancer is gastric cancer, small bowel cancer, colon cancer or rectal cancer, leukemia or lymphoma.

In a separate embodiment of the above-described methods, the tumor is a breast cancer. In another embodiment, the tumor is a ovarian cancer. In a still another embodiment, the tumor is selected from a group consisting of prostate cancer, lung cancer, melanoma, cervical carcinoma, pancreatic cancer, sarcoma, hepatoma and gallbladder cancer.

Finally, this invention provides a method for potentiating apoptosis in tumor cells comprising contacting the cancerous cells with an effective amount of a specific protein kinase C inhibitor capable of potentiating apoptosis during or prior to the treatment of an antitumor therapeutic agent.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

First Series of the Experiments

Materials and Methods

Cell culture

Early passage human gastric cancer cell lines SK-GT-5 and MKN-74 were established and characterized as described previously (13,14). All cultures were maintained at 37° C. in Eagles minimum essential media (MEM) supplemented with 20% fetal calf serum in an humidified 5% $CO_2$ atmosphere; the cultures tested negative for Mycoplasma species.

Determination of Apoptosis

Apoptosis was measured by two different methods: (i) Quantitative fluorescent microscopy (QFM) of nuclear changes induced by apoptosis, as determined by bisbenzimide trihydrochloride (Hoescht-33258) staining of nuclear chromatin (15), and (ii) a terminal deoxynucleotidyl transferase (TdT) assay that labels the 3'-OH ends of DNA fragments produced in apoptotic cells (16). Cells were treated according to one of several protocols: (i) no drug (control) for 24 hours; (ii) safingol alone for 24 hours at 50 $\mu$M, a concentration representing the highest non-toxic dose for SK-GT cells (as determined by cell proliferation studies with [$^3$H]-thymidine (4)) and slightly exceeding the concentration (i.e., 30 $\mu$M) which inhibits PKC enzyme activity by 50% in vitro; (iii) Mitomycin-C alone at 5 $\mu$g/ml for 24 hours; (iv) a combination of safingol (50 $\mu$M) and Mitomycin-C (5 $\mu$g/ml) for 24 hours; (v) safingol (50 $\mu$M) alone for 1 hour, followed by an immediate wash out of the drug with fresh MEM, and then an additional 24 hours of MMC (5 $\mu$g/ml) exposure; (vi) safingol (50 $\mu$M) with 1 ng/ml 3-phorbol 12-myristate 13-acetate (PMA) for 1 hour, followed by an immediate wash out of the drug with MEM and 24 hours of MMC (5 $\mu$g/ml) exposure; and (vii) either safingol (50 $\mu$M) alone or PMA (1 ng/ml) alone for 1 hour, followed by drug washout with MEM and 24 hours of exposure to media without drug. The dose of MMC used was based on proliferating studies with [$^3$H]-thymidine (14, and unpublished data) indicating 20% inhibition of cell proliferation. MMC was diluted in water. A stock safingol solution was constituted in DMSO and was subsequently diluted at least 1:100 in media for all experiments. This dilute concentration of DMSO does not induce apoptosis or inhibit cell proliferation in these cell lines (unpublished data). For QFM determinations, the cells were fixed in 3% paraformaldehyde and incubated at room temperature for 10 minutes. The fixative was removed and the cells were washed with 1× PBS, resuspended in 20 $\mu$l 1× PBS containing only 8 $\mu$g/ml of bisbenzimide trihydrochloride (Hoechst #33258), and incubated at room temperature for 15 minutes. Aliquots of the cells (10 $\mu$l) were placed on glass slides coated with 3-amino-propyl-triethoxysilane, and duplicate samples of 500 cells each were counted and scored for the incidence of apoptotic chromatin condensation using an Olympus BH-2 fluorescence microscope equipped with a BH2-DM2U2UV Dich. Mirror Cube filter (Olympus, Lake Success, N.Y.). For the TdT assays, the ApopTag Kit (Oncor, Gaithersburg, Md.) was used. This method employs a fluoresceinated antidigoxigenin antibody directed against nucleotides of digoxigenin-11-dUTP (d-dUTP) which are catalytically added to the 3-ends of fragmented DNA by TdT. Briefly, $1-2 \times 10^6$ cells were washed and fixed with 1% paraformaldehyde. The fixed cells were incubated in a reaction mixture containing TdT and d-dUTP for 30 minutes at 37° C. Stop/wash buffer was added, and the cells were resuspended in 100 $\mu$l of fluorescinated anti-digoxigenin antibody for 30 minutes at room temperature. The cells were then washed with 0.1% Triton X-100 and counterstained with propidium iodide (PI) solution. Green (d-dUTP labeled DNA strand breaks) and red (PI staining for total DNA content) fluorescence of individual cells were measured on a FACScan flow cytometer (Becton Dickinson, San Jose, Calif.). The resulting bivariate plots enabled the detection of apoptotic events within the cell cycle. The $R_1$ cursor was set using the control specimen to define normal levels of green fluorescence (i.e., basal levels of apoptosis). Cells with fluorescence above the $R_1$ cursor were considered apoptotic. The data from 10,000 cells were collected and analyzed using CellFit and LYSYS software (Becton Dickinson).

Statistical analysis

All experiments were done in duplicate and were repeated at least three times unless otherwise indicated. The statistical significance of the experimental results was determined by the two-sided Student's t test.

EXPERIMENTAL RESULTS

Effect of safingol and MMC on inducing apoptosis in SK-GT-5 and MKN-74 cells.

Figure 1A:
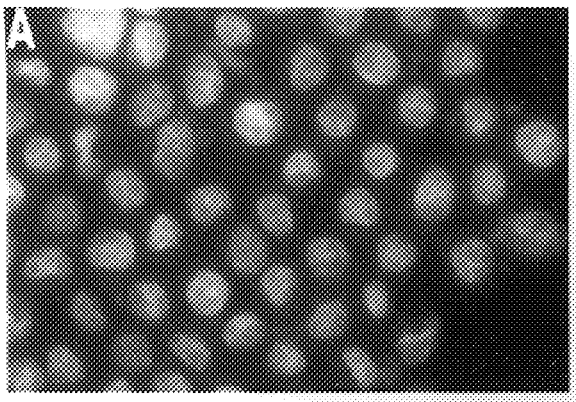
FIG. 1. Photomicrographs of representative fields of SK-GT-5 cells (mutant for p53) stained with bibenzimide trihydrochloride (Hoescht-33258) to evaluate nuclear chromatin condensation (i.e., apopotosis) after treatment for 24 hours with no drug (panel A), safingol alone (50 $\mu$M, panel B), MMC alone (5 $\mu$g/ml, panel C), or the combination of safingol (50 $\mu$M) and MMC (5 $\mu$g/ml) (panel D).
Figure 1B:
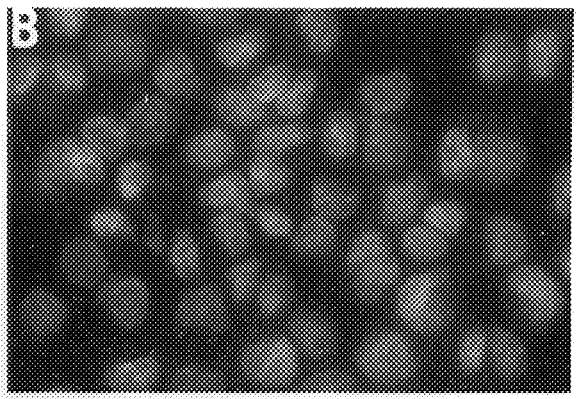
Figure 1C:
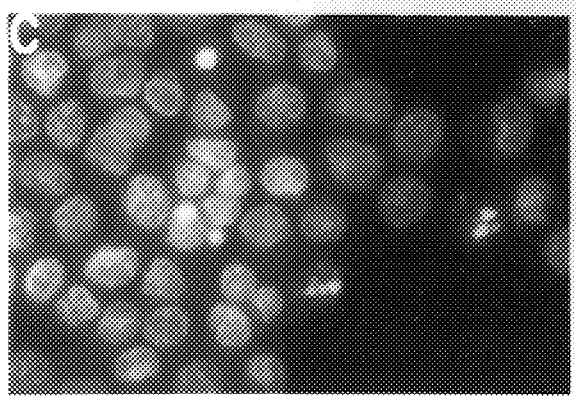
Figure 1D:
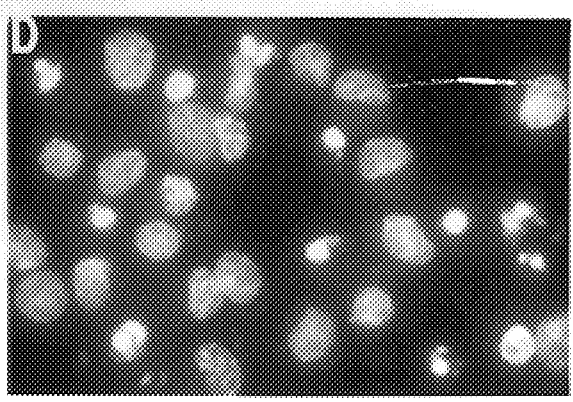
Figure 2:
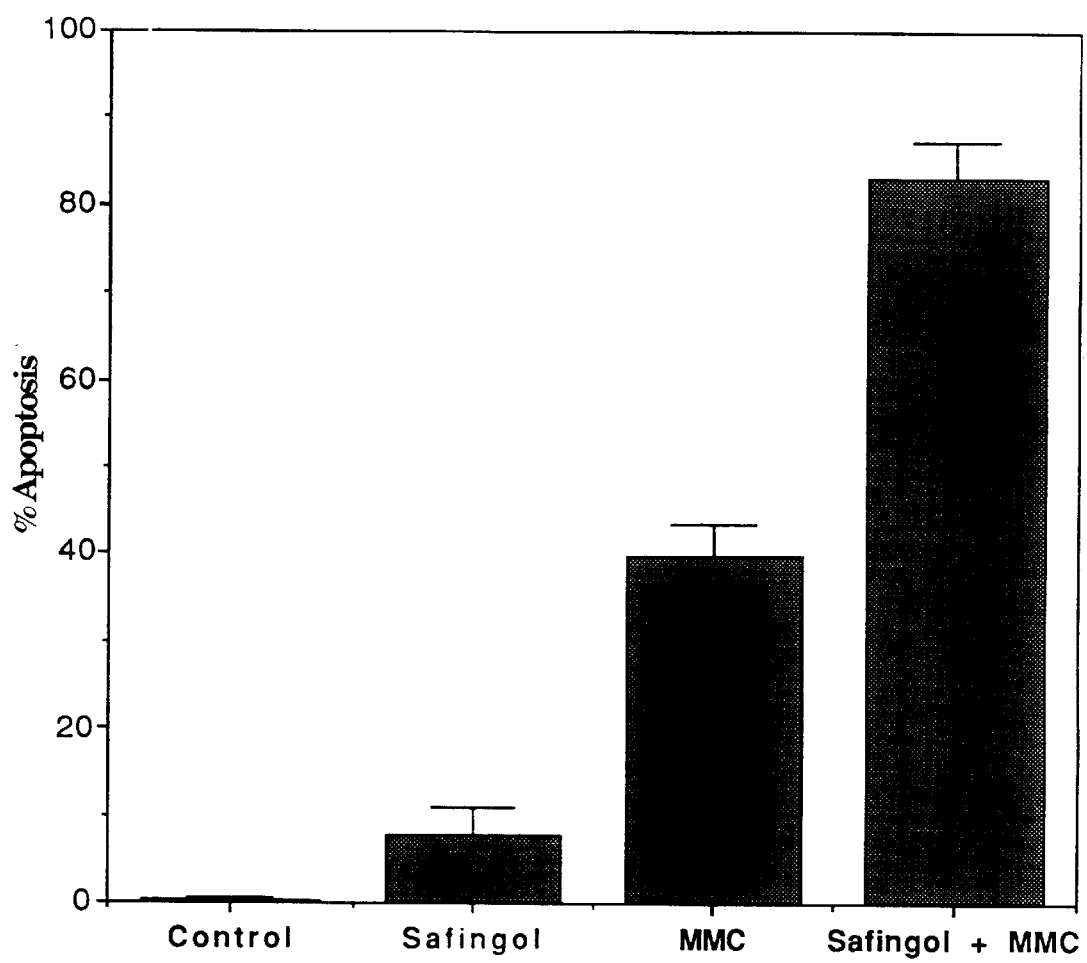
FIG. 2. Induction of apoptosis in MKN-74 cells (a wild-type for p53) with safingol alone (50 $\mu$M), MMC alone (5 $\mu$g/ml), or safingol (50 $\mu$M) in combination with MMC (5 $\mu$g/ml). Cells were counted and scored for apoptotic chromatin condensation by the QFM method described in the "Material and Methods" section. Bars represent mean number of cells counted that undergo apoptosis as a percentage of 500 total cells randomly counted in duplicate samples, ±SD.

SK-GT-5 cells, which have a mutated p53 gene (14) and have deficient p53 function (unpublished data), were treated with safingol in the presence or absence of MMC for 24 hours. Cells were counted and scored for condensed nuclear chromatin, and representative photomicrographs are shown in FIG. 1. Treatment with safingol alone (Panel B) did not induce significant levels of apoptosis (2%±1) when compared with untreated controls (<1%, Panel A). However, the combination of safingol and MMC (Panel D) significantly increased the percentage of cells undergoing apoptosis from 18%±1 with MMC alone (Panel C) to 39%±1 with the drug combination (p <0.001). Treatment of SK-GT-5 cells with safingol for only 1 hour prior to 24 hours of treatment with MMC resulted in an increase in apoptosis (44%±4% of exposed cells) that was essentially equivalent to that which was observed with concomitant exposure of the cells to the two drugs for the entire 24 hour interval (data not shown). MKN-74 cells, which are a wild- type for p53, were subjected to the same treatments. As shown in FIG. 2, cell counts of MKN-74 cells following treatment with safingol alone indicated no significant induction of apoptosis (8%±3) when compared to untreated controls (<1%). However, the combination of safingol and MMC significantly increased the percentage of cells undergoing apoptosis from 40%±4 with MMC alone to 83%±4 with safingol and MMC together (p<0.005).

Identifying gastric cancer cells undergoing apoptosis by the TdT assay

MKN-74 cells were treated in the same manner and analyzed by combining the TdT assay and flow cytometry. With this approach, apoptotic cells were identified as those shifting above the $R_1$ region of the contour plot. FIG. 3 shows that MKN-74 cells incubated with safingol alone for 24 hours (Panel B) had the same levels of green fluorescence as the control cells (Panel A), i.e., essentially no apoptosis. Treatment with MMC alone for 24 hours (Panel C) resulted in the cells exhibiting increased green fluorescence (sorted above the $R_1$ region), indicating development of apoptosis.

The results in Panel C indicate that the apoptotic cells, after MMC treatment, alone are derived from those that were in the $G_0/G_1$ and S phases of the cell cycle. However, exposure of the MKN-74 cells to the combination of MMC and safingol for 24 hours (Panel D) resulted in an even greater increase in cells exhibiting elevated green fluorescence. In the presence of safingol and MMC, apoptotic cells appear to arise out of all phases of the cell cycle. Similar results were also observed for SK-GT-5 cells (data not shown).

Effect of PMA on apoptosis induced by safingol and MMC

PMA activates PKC by binding to its regulatory site (17). Safingol, as a sphingosine, inhibits PKC activity by interfering with the function of PKC's regulatory domain (18). Therefore, applicants hypothesized that if the potentiation of MMC-induced apoptosis by safingol is mediated by inhibition of PKC, then PMA should abrogate this effect. As shown in FIG. 4, treatment of SK-GT-5 cells with either safingol or PMA alone had essentially no effect on inducing apoptosis. Preexposure of the cells to safingol alone for one hour followed by MMC for an additional 24 hours induced a significant increase in apoptosis from 36%±4 with a 24 hour exposure of MMC alone to 55%±1 with the combination (p<0.01). However, under the conditions in which cells were preexposed to PMA and safingol together for one hour before MMC, the induction of apoptosis was inhibited to the level observed for MMC alone.

Experimental Conclusion

The present studies show that safingol potentiates the cytotoxic effect of MMC in two human gastric cancer cell lines which differ in their baseline sensitivity to MMC and in their p53 status. Neither cell line expresses P-glycoprotein (unpublished data). As shown by bisbenzimide trihydrochloride staining and the TdT assay, safingol alone did not dramatically induce apoptosis in either the MMC-sensitive MKN-74 cells, which have a wild-type p53 function, or the MMC-resistant SK-GT-5 cells, which are deficient for p53. In addition, the typical oligonucleosomal base pair fragments (DNA "ladders") were not induced by safingol under the conditions tested (data not shown). When exposed to MMC alone, apoptosis was induced in both cell lines although to different degrees. Addition of safingol potentiated this apoptotic response approximately 2-fold in both cell lines. Applicants have observed a similar potentiation of apoptosis by safingol with other chemotherapeutic agents, including doxorubicin.

Recent studies have suggested a link between the induction of apoptosis and a p53-dependent pathway (19). Cells which express wild-type p53 are capable of undergoing apoptosis after exposure to common chemotherapeutic agents or ionizing radiation; whereas cells with mutated or deleted p53 are resistant, avoiding apoptosis and continuing to replicate. In view of the prevalence of p53 mutations in solid tumors, overcoming this form of resistance should greatly enhance the efficacy of cancer chemotherapy. Applicants' studies demonstrate that safingol sensitizes gastric cancer cells, with either wild-type or mutated p53, to the induction of apoptosis by MMC. These results suggest that the effect of safingol on enhancing MMC-induced apoptosis may be independent of the p53 status of the cells. The existence of a p53- independent pathway for growth arrest has been reported (20). Further studies to define the effects of safingol, especially as it pertains to PKC and steps independent of p53 in the cell cycle, are a subject of ongoing investigation.

The mechanism of action of safingol may be associated with its anti-PKC effect. Safingol is a highly specific inhibitor of PKC (4). Safingol inhibits PKC activity by binding to its amino-terminal regulatory domain (18), which contains PKC's phorbol ester binding site (17). PKC inhibitors, such as staurosporine, inhibit PKC activity presumably by binding to the catalytic domain at the C-terminus of PKC (21). The use of staurosporine has been associated with a high level of nonspecific toxicity due to the fact that the catalytic domain of PKC is highly homologous to similar domains found in other protein kinases (e.g., pp60$^{v-src}$, cAMP-dependent protein kinase A, and casein kinase), each of which is critical for normal cellular functions (21,22). In contrast, safingol shows no toxicity in vivo at concentrations that effectively inhibit PKC (5). The fact that PMA, which competes with safingol for the regulatory binding site of PKC, effectively abrogated the safingol effect of potentiating MMC-induced apoptosis, supports the hypothesis that this process is a PKC-dependent event.

Sphingosines, including dimethylsphingosine, have been reported to induce DNA fragmentation as single agents (23). In applicants' studies, safingol (L-threo-dihydrosphingosine) alone did not induce apoptosis when administered to gastric cancer cells. This observation was confirmed by histochemical staining, the TdT assay, and the failure to induce DNA "ladders" under identical experimental conditions. The reason for the different effects of sphingoid bases on inducing apoptosis remains unexplained. The different results may depend on which enantiomer of sphingosine is used, since it appears that different sphingosine enantiomers induce varying physiological responses. For example, D-erythro-sphingosine induces dephosphorylation of the retinoblastoma gene product in human T-cells; whereas the racemic mixture of DL-threo-sphingosine does not (24). Thus, the actual sphingosine used may be critical in evaluating its ability to induce apoptosis. This hypothesis is currently being tested. Nevertheless, the inability of safingol alone to induce apoptosis supports the in vivo observation of the lack of single agent activity against tumor xenografts. The anti-cancer effect of safingol in vivo depends on concomitant exposure with a standard chemotherapeutic agent.

Recent investigations into the elements that regulate apoptosis have provided evidence for the existence of a balance between pro- and anti-apoptotic signaling that determines the final choice. This balance appears to be reciprocally regulated through the sphingomyelin signal transduction pathway that mediates the pro-apoptotic signals (15,25) and the activation of the phosphoinositide-PKC pathway that mediates the anti-apoptotic signals (26,27). Thus, inhibition of the phosphoinositide-PKC pathway by the PKC-specific inhibitor safingol in combination with MMC may be sufficient to tip the balance in favor of pro-apoptotic signals.

The demonstration that safingol potentiates chemotherapy-induced apoptosis, presumably via inhibition of PKC, may have important clinical implications in view of its recent introduction into clinical trials as a specific PKC inhibitor, in combination with chemotherapy. This agent is well-tolerated, and serum levels of safingol can be achieved in patients approximating those that potentiate the effects of chemotherapy in tumor-bearing animals (28).

While alternative mechanisms for safingol action may exist (i.e., inhibition of DNA repair), applicants' studies indicate that safingol may represent a new class of therapeutic agents that potentiate the cytotoxic effects of anti-cancer chemotherapy through the inhibition of PKC and the enhancement of apoptosis. Of particular importance is the finding that safingol is effective even in tumor cells that have a mutated p53 and exhibit relative resistance to chemotherapy. Hence, the use of safingol may provide a new approach to overcoming drug resistance in tumors that are resistant to chemotherapy by virtue of lacking p53 function.

REFERENCES OF THE FIRST SERIES OF EXPERIMENTS

1. Nishizuka Y. The role of PKC in cell surface signal transduction and tumor promotion. Nature, 308: 693–698, 1984.
2. Housey G. M., Johnson M. D., Hsiao W. L. W., O'Brian C. A., Murphy J. P., Kirschmeirer P., and Weinstein I. B. Overproduction of protein kinase C causes disordered growth control in rat fibroblasts. Cell 52: 343–354, 1988.
3. Schwartz, G. K., Redwood S. M., Ohnuma T., Holland J. F., Droller M. J., and Liu B. C. S. Inhibition of invasion of invasive human bladder carcinoma cells by protein kinase C inhibitor staurosporine. J. Natl. Cancer Inst. 82: 1753–1756, 1990.
4. Schwartz G. K., Jiang J., Kelsen D., and Albino A. P. Protein kinase C: a novel target for inhibiting gastric cancer cell invasion. J. Natl. Cancer Inst. 85: 402–407, 1993.
5. Susick R. L., Bozigian H. P., Kurtzberg J., Adams L. M., Weiler M. S., Harrison S. D., and Kedderis L. B. Combination toxicology studies with the chemopotentiating agent SPC-100270 (a PKC inhibitor) and chemotherapeutic agent. Proc. Amer. Assoc. Cancer Res. 34: A2444, 1993.
6. Adams L. M., Dykes D., Harrison S. D., Saleh J., and Saah L. Combined effect of the chemopotentiator SPC-100270, a protein kinase C inhibitor, and doxorubicin or cisplatin (Cis) on murine isografts and human tumor xenografts. Proc. Amer. Assoc. Cancer Res. 34:A2448, 1993.
7. Sachs C. W., Safa A., and Fine R. L. Inhibition of protein kinase C by Safingol is associated with chemosensitization of multidrug resistant MCF-7 cells. Proc. Amer. Assoc. Cancer Res. 35:447, 1994.
8. Adams L. M., Cofield D. J., Seldin J. C., Kitchen P. A., et al. Effect of the protein kinase C (PKC) inhibitor SPC-100270 on drug accumulation and cytotoxicity in drug resistant and sensitive tumor cell in vitro. Proc. AACR 34:410, 1993.
9. Evans D. L. and Dive C. Effects of cisplatin on the induction of apoptosis in proliferating hepatoma cells and nonproliferating immature thymocytes. Cancer Res. 53: 2133–2139, 1993.
10. Jarvis W. D., Turner A. J., Povirk L. F., Traylor R. S., and Grant S. Induction of apoptotic DNA fragmentation and cell death in HL-60 human promyelocytic leukemia cells has been reported for pharmacological inhibitors of protein kinase C. Cancer Res. 54: 1707–1714, 1994.
11. McConkey D. J., Hartzell P., Jondal M., and Arrenius S. Inhibition of DNA fragmentation in thymocytes and isolated thymocyte nuclei by agents that stimulate protein kinase. J. Biol. Chem. 264: 13399–13402, 1989.
12. Haimovitz-Friedman A., Balaban N. A., McLoughlin M., Ehleiter D., Michaeli J., Vlodavsky I., and Fuks Z. PKC mediates basic fibroblast growth factor of endothelial cells against radiation-induced apoptosis. Cancer Res. 54: 2591–2597,1994.
13. Altorki N., Schwartz G. K., Blundell M., Davis D., Kelsen D., and Albino A. Characterization of cell lines established from human gastric-esophageal adenocarcinomas: Biologic phenotype and invasion potential. Cancer 72: 649–657, 1993
14. Nabeya Y., Loganzo F., Maslak P., Lai L., et al. The mutational status of p53 protein in gastric and esophageal adenocarcinoma cell lines predicts sensitivity to chemotherapeutic agents. Int. J. Cancer 64: 1–10, 1994.

15. Haimovitz-Friedman A., Chu-Cheng K., Ehleiter D., Persaud R. S. et al. Ionizing radiation acts on cellular membranes to generate ceramide and initiate apoptosis. J. Exp. Med. 180: 525–535, 1994.
16. Schmitz G., Walter T., Serbel R., and Kessle C. Nonradioactive labeling of oligonucleotides in vitro with the hapten digoxigenin by tailing with terminal transferase. Anal. Biochem. 192: 222–231, 1991.
17. Blumberg P. M. Protein kinase C as the receptor for the phorbol ester tumor promoter: Sixth Rhoads memorial award lecture. Cancer Res. 48: 1–8, 1988.
18. Hannun Y. A., Loomis C. R., Merrill A. H., and Bell R. M. Sphingosine inhibition of protein kinase C activity and of phorbol dibutyrate binding in vitro and in human platelets. J. Biol. Chem. 261: 12602–12609, 1986.
19. Lowe S. W., Ruley H. E., Jack T., Housman D. E. p53-Dependent apoptosis modulates the cytotoxicity of anticancer agents. Cell 74: 957–967, 1993.
20. Johnson M., Dimitrov D., Vojta P. J., Barrett J. C., Noda A., Pereira-Smith O., and Smith J. Evidence for a p53-independent pathway for upregulation of SDI1/CIP1/WAF1/p21 RNA in human cells. Mol Carcinogenesis 11: 59–64, 1994.
21. Tamaoki T. and Nakano H. Potent and specific inhibitors of PKC or microbial origin. Biotech. 8: 732–735, 1990.
22. Nakano H., Kobayashi, E., Takahashi, I., Tamaoki, T., Kuzuu, Y., and Iba, H. Staurosporine inhibits tyrosine-specific protein kinase activity of Rous sarcoma virus transforming protein. J. Antibiot (Tokyo) 40:706–708, 1987.
23. Ohta H., Sweeney E. A., Masamune A., Yatomi Y., Hakomori S., and Igarashi Y. Induction of apoptosis by sphingosine in human leukemic HL-60 cells: a possible endogenous modulator of apoptotic DNA fragmentation occurring during phorbol ester-induced differentiation. Cancer Res. 55: 691–697, 1995.
24. Choa R., Khan W., and Hannun Y. A. Retinoblastoma protein dephosphorylation induced by D-erythro-sphingosine. J. Bio. Chem. 267: 23459–23462, 1992.
25. Jarvis W. D., Kolesnick R. N., Fornari F., Traylor R. S., Gewirtz D. A. and Grant S. Induction of apoptotic DNA damage and cell death by activation of the sphingomyelin pathway. Proc. Natl. Acad. Sci. U.S.A. 91:73–77, 1994.
26. Obeid L. M., Linardic C. M., Karolak L. A., and Hannun Y. A. Programmed cell death induced by ceramide. Science 259:1769–1771, 1993.
27. Jarvis W. D., Fornari F. A., Browning J. L., Gewirtz D. A., Kolesnick R. N., and Grant S. Attenuation of ceramide-induced apoptosis by diglyceride and pharmacological activators of protein kinase C in human myeloid leukemia cells. J. Biol. Chem. 268:31685–31692, 1994.
28. Schwartz G. K., Ward D., Saltz L. Casper E., et al. A phase I study of the protein kinase C specific inhibitor safingol alone and in combination with doxorubicin. Proc. Amer. Soc. Clin. Onc. 14:1557,1995.

Second Series of Experiments

Applicants' long term objective is to improve clinical cancer therapy by developing a new therapeutic strategy in the treatment of human malignancies which utilizes protein kinase C (PKC) as a target for enhancing chemotherapy induced apoptosis in tumor cells. Study designs will be based on applicants' pre-clinical data indicating that PKC represents a major new target in the enhancement of chemotherapy induced apoptosis of human gastric cancer cells that are resistant to chemotherapy by virtue of a mutation in p53. Applicants' hypothesis is that the activation of PKC inhibits the induction of chemotherapy induced apoptosis and that this can be overcome by utilizing PKC inhibitors in conjunction with chemotherapy. This process may be associated with other mechanisms including alterations in cell cycle progression and modulation of cyclin dependent kinase 2 (cdk2) activity. Applicants' specific immediate and long term aims are:

1. To develop an integrated clinical program with PKC inhibitors in combination with chemotherapy that uses laboratory correlates (PKC activity, cdk2 activity, and terminal deoxynucleotidyl transferase (TdT) activity in tumor tissues and leukocytes) as putative surrogate end-points of activity. The immediate goal will be to complete two current phase I clinical trials with the PKC specific inhibitor L-threo-dihydrosphingosine (safingol) in combination with (i) doxorubicin (DOX) and (ii) cisplatin with the plan to take this to a phase II study in gastric cancer; and to initiate additional clinical trials with combinations of chemotherapy and other PKC inhibitors including UCN-01, flavopiridol, and bryostatin.

2. To perform laboratory studies with human gastric, breast, and ovary cancer cells to: i) study a variety of new PKC inhibitors currently under pre-clinical development as inducers of apoptosis in combination with chemotherapy; ii) define the optimal conditions in which to combine safingol, UCN-01, flavopiridol, and bryostatin with chemotherapy for future clinical development; and iii) further examine cdk2 in vitro and to identify other related cell cycle dependent proteins associated with induction of apoptosis and the inhibition of PKC.

3. To determine whether a specific PKC isoform may be a critical target for drug development in induction of apoptosis with chemotherapy by: (i) testing whether an antisense for PKCα in combination with MMC has superior anti-tumor activity against human gastric cancer cells when compared to either agent alone or to a PKC missense with MMC; (ii) testing PKC antisense against other PKC specific isoforms in combination with chemotherapy; (iii) studying in gastric cancer cells whether any of the PKC isoforms are being preferentially inhibited during the induction of apoptosis.

Background

Recent studies have indicated a link between the induction of apoptosis (programmed cell death) and p53 expression (1). Cells which express wild-type p53 are capable of undergoing apoptosis after exposure to common chemotherapeutic agents or ionizing radiation; whereas cells with mutated or deleted p53 are resistant, avoiding apoptosis and continuing to replicate. A major hurdle for cancer chemotherapy is how to overcome this form of drug resistance. It has been suggested that the anti-tumor activity of many chemotherapeutic agents (e.g., cisplatin and etoposide) is a consequence of their induction of apoptosis (1,2). Recent investigations into the elements that regulate apoptosis have provided evidence for the existence of a balance between pro- and anti-apoptotic signaling that determines the final choice. Applicants' hypothesis is that this balance appears to be reciprocally regulated through the sphingomyelin signal transduction pathway that mediates the pro-apoptotic signals (3,4) and the activation of the phosphoinositide-Protein Kinase C (PKC) pathway that mediates the anti-apoptotic signals (5–7). Thus, inhibition of the phosphoinositide-PKC pathway by the PKC specific inhibitors may be sufficient to tip the balance in favor of pro-apoptotic signals. Consequently, PKC may represent a novel target for anti-cancer therapy in gastric cancer.

In the United States adenocarcinoma of the stomach is the 8th leading cause of death from cancers. It is estimated that over 24,000 new cases will be diagnosed in 1995 and this will be associated with approximately 14,000 deaths (8). Even though the number of newly diagnosed patients with gastric cancer in the United States has remained essentially constant over the past 10–15 years, the incidence of proximal gastric cancers, which is a much more aggressive form of this disease, appears to be rising rapidly in this country (9). This disease appears to affect young males and its incidence is independent of socio-economic status. There have been no identifiable factors to account for the dramatic rise in tumors of the gastric cardia or gastro-esophageal junction, but the rate of rise exceeds that of lung cancer or melanoma for this age group. Adjuvant chemotherapy for this disease has not had a meaningful impact on survival (10) and in the metastatic setting objective response rates are low and generally brief.

The tumors of many of the patients with gastric cancer are resistant to the most active chemotherapeutic agents. The basis of drug resistance in these disease has not been well defined. The expression of the multi-drug resistant gene (mdr1), which encodes the P-glycoprotein, is low (11), suggesting alternate mechanisms of drug resistance. For gastric cancer applicants have been successful in establishing five long-term cell lines, SK-GT-1, SK-GT-2, SK-GT-4, SK-GT-5, and SK-GT-6 for Sloan Kettering Gastric Tumor (12,13) none of which express P-glycoprotein (14). Yet, all these tumors are resistant to chemotherapy and to the induction of apoptosis. Applicants have reported that the relative sensitivity of these gastric cancer cells to chemotherapy is influenced by their p53 status (14). These results are summarized below with the relative resistance (% cell survival by clonogenic assay/% cell survival of MKN-74 cells, wild-type for p53, by clonogenic assay) to 10 $\mu$g/ml Cisplatin (CDDP), 5 $\mu$g/ml Mitomycin-C (MMC), and 50 $\mu$M 5-Fluorouracil (5-FU) noted:

| Cell line/ site | p53 mutational status/ codon | Fold-Increase in Resistance Relative to MKN-74 (p53$^{wt}$) | | |
|---|---|---|---|---|
| | | CDDP | MMC | 5-FU |
| SK-GT-1/ GE junction | 17 base pair deletion/57–62 | 21X | 166X | 11X |
| SK-GT-2/ fundus | CGC to CAC/ 175 | 11X | 106X | 12X |
| SK-GT-4/ GE junction | CGC to CAC/ 175 | N.A.* | N.A. | N.A. |
| SK-GT-5/ GE junction | GAC to GAG/ 281 | 12X | 55X | 6X |
| MKN-74/ lymph node | No mutation | 1X | 1X | 1X |
| NU-GC-4/ lymph node | No mutation | 2X | 10X | 0.6X |

*Not assayed

Applicants' results indicate that the that the MKN-74 and the NU-GC-4 cells, which are wild-type for p53, are exhibit sensitivity to chemotherapy (e.g. CDDP, 5-FU, and MMC) and to the induction of apoptosis; whereas the SK-GT cell lines which have a mutation in p53 exhibit resistance to chemotherapy and to the induction of apoptosis (14).

Since the activity of PKC has been reported to be increased in gastric cancer cells (15) and since p53 mutation is prevalent in gastric tumors (16), applicants believed applicants could use these gastric cancer cell lines to test applicants' hypothesis that the activation of PKC inhibits the induction of chemotherapy induced apoptosis and that inhibiton of PKC can enhance chemotherapy induced apoptosis even in tumor cells with a p53 mutation. The selection of a PKC inhibitor for these studies ultimately depended on its specificity for PKC. The "classic" PKC inhibitor, staurosporine (STSN), inhibits PKC activity in nanomalar concentrations presumably by binding to the enzyme's catalytic site (17). Members of the PKC family are characterized by a unique amino-terminal regulatory domain containing co-factor binding sites and a carboxyl-terminal catalytic domain which is homologous to that of these other protein kinases (18,19). However, STSN is also exceptionally toxic (18). The concentrations of STSN that inhibit enzyme activities of PKC, pp60$^{v-src}$ tyrosine kinase and cAMP-dependent protein kinase A by 50% (IC$_{50}$), as well as other enzymes that are critical for normal cellular functions, are all within a ten-fold range of concentration (17,20). The toxicity of STSN then appears to be related to its non-selectivity in view of the considerable homology PKC shares with these other protein kinases (20). Due to this lack of specificity, the development of a PKC inhibitor for clinical trials will ultimately depend on an agent that is either highly specific for the catalytic domain of PKC or inhibits PKC by mechanisms that are independent of the catalytic site. A series of PKC inhibitors are now in pre-clinical development. These agents and the site by which they inhibit PKC are summarized in the table below:

| Drug | Chemical derivative | Site of PKC inhibition |
|---|---|---|
| Safingol (5) | L-threo-dihydrosphingosine | Regulatory |
| UCN-01 (21) | 7-OH-staurosporine | Catalytic |
| RO32-0432 (22) | Bisindolylmaleimide tertiary amine | Catalytic |
| Bryostatin 1 (23) (prolonged exposure only) | Macrocyclic lactone | Regulatory |
| Flavopiridol (24) (in $\mu$M concentrations) | Flavone L86-8275 | Catalytic (?) |

Safingol, as a sphingosine (25), is a highly specific PKC inhibitory by virtue of its interfering with the function of the enzyme's regulatory domain (5). The concentration of safingol that inhibits PKC enzyme activity by 50% (I$_{50}$) is 33 $\mu$M but exceeds 218 $\mu$M for the inhibition of cyclic-adenosine monophosphate-dependent protein kinase A, creatinine phosphokinase and casein kinase. As a single agent safingol has been shown to have a negligible impact on tumor growth in vivo. However, the combination of safingol with doxorubicin or cisplatin substantially potentiates the anti-tumor effects of these drugs (26). Based on these observations, safingol, used in combination with doxorubicin, has become the first PKC specific inhibitor to enter clinical trials, MSKCC IRB protocols #93–44 (27), and a second trial combining safingol with cisplatin has been approved protocol, MSKCC protocol #94–115. Non-toxic doses of safingol have been given to patients that approach concentrations necessary to inhibit PKC in vivo and to induce chemosensitization in animals in (see Preliminary Results below).

It has been suggested that the mechanism by which safingol potentiates chemotherapeutic agents is by inhibition of P-glycoprotein phosphorylation and reversal of the multidrug resistant (mdr) phenotype (28). While this hypothesis can explain the synergism achieved with combinations of safingol and doxorubicin, it does not explain the synergism reported for combinations of safingol with drugs that are not believed to produce resistance by the mdr mechanism (e.g., cisplatin) (28), nor does it explain safingol-induced effects that occur in tumor cell lines that do not express the P-glycoprotein (29). Therefore, pathways other than P-glycoprotein inhibition are likely to be involved in the safingol-mediated enhancement of chemotherapy. Applicants proposed that safingol-mediated potentiation of chemotherapy might be attributed to its PKC inhibitory effect, subsequently leading to increased apoptosis after drug-induced damage. In order to test this hypothesis applicants initially sought to determine the extent to which safingol by itself, or in combination with MMC would promote apoptosis in gastric cancer cells. Furthermore, applicants investigated whether the p53 status of these cells influences the development of apoptosis after treatment with safingol and MMC (5).

For these initial studies applicants used the gastric cancer cell lines SK-GT-5 cells and MKN-74. Neither cell line expresses P-glycoprotein. These studies (see PRELIMINARY RESULTS) show that safingol potentiates the cytotoxic effect of MMC in two human gastric cancer cell lines which differ in their baseline sensitivity to MMC and in their p53 status. Neither cell line expresses P-glycoprotein (unpublished data). Safingol alone did not dramatically induce apoptosis in either the MMC-sensitive MKN-74 cells, which have a wild-type p53 function, or the MMC-resistant SK-GT-5 cells, which are deficient for p53. In addition, the typical oligonucleosomal base pair fragments (DNA "ladders") were not induced by safingol under the conditions tested (data not shown). When exposed to MMC alone, apoptosis was induced in both cell lines although to different degrees. Addition of safingol potentiated this apoptotic response approximately 2-fold in both cell lines. Applicants have observed a similar potentiation of apoptosis by safingol with other chemotherapeutic agents, including doxorubicin.

In order to test whether the effect of safingol in inducing apoptosis was due to its anti-PKC effect, applicants performed comparable studies with safingol in the presence of the phorbol ester, 3-phorbol 12-myristate 13-acetate (PMA), which activates PKC by binding to its amino-terminal regulatory domain (19). Safingol inhibits PKC activity by interfering with the function of PKC's regulatory domain (5). Therefore, applicants hypothesized that if the potentiation of MMC-induced apoptosis by safingol is mediated by inhibition of PKC, then PMA should abrogate this effect. In applicants' studies with the gastric cancer cells, PMA effectively abrogated the safingol effect of potentiating MMC-induced apoptosis in this cells, supporting the hypothesis that this process is a PKC-dependent event (5).

Applicants' studies demonstrate that safingol sensitizes gastric cancer cells, with either wild-type or mutated p53, to the induction of apoptosis by MMC. This suggests that the effect of safingol on enhancing MMC-induced apoptosis is independent of the p53 status of the cells. The existence of a p53 independent pathway for apoptosis has been reported (30). In order to identify apoptotic cells in the cell cycle applicants have treated MKN-74 and SK-GT-5 cells with MMC and safingol and analyzed the cells by combining the TdT assay and flow cytometry. By this approach applicants have reported that in the presence of safingol and MMC apoptotic cells arise out of all phases of the cell cycle ($G_0/G_1$, S, and $G_2/M$) (5). This is in contrast to treatment with safingol alone, in which there are no apoptotic cells detected by this method, and to treatment with MMC alone in which apoptotic cells are derived from $G_0/G_1$ and S (but to a significantly less degree than the combination therapy). Thus, it appears that safingol may effect more than one point regulating progression through the cell cycle.

The PKC inhibitor UCN-01 has been reported to enhance anti-tumor activity of MMC against xenografted human colon carcinoma Co-3 cells in nude mice (31). Similar to safingol, UCN-01 induces apoptosis and has effects on the cell cycle (32). Both agents induce apoptosis in all phases of the cell cycle. However, in contrast to safingol, this effect is observed with UCN-01 alone and does not require the presence of chemotherapy (though the effect on apoptosis of combining UCN-01 with chemotherapy has not been tested). This difference between UCN-01 and safingol may reflect the differences in cell lines tested (Jurkat T lymphoblastic leukemia cells for UCN-01 and SK-GT gastric cells for safingol) or it may be a direct result of the specificity of each PKC inhibitor. For example, UCN-01 is a more potent inhibitor of PKC than safingol; whereas safingol, by virtue of interfering with PKC's regulatory domain, is more specific. Alternatively, these PKC inhibitors may have different effects, either alone or in combination with chemotherapy, on cell-cycle specific events.

Progression through the cell cycle is regulated by cyclin-dependent kinases (cdks), the activation of which involves both the binding of a cyclin partner and phosphorylation and dephosphorylation of specific threonine/tyrosine residues. In particular cdk2 is activated by the phosphorylation of threonine-160 and dephosphorylation of tyrosine-15 and threonine-14 (33). The activation of cdk2 complexes is necessary for the $G_1/S$ progression of the cell cycle, and the inappropriate activation of cdks has been associated with apoptosis (34). The effect of UCN-01, as a PKC inhibitor, on cdk2 activity has been studied in Jurkat T leukemia cells (32). These results indicate that UCN-01 increase the activity of cdk2 in association with a decrease in tyrosine-15 phosphorylation. Similar studies has been performed with the PKC activator, bryostatin 1, which has undergone phase I evaluation as a single agent (35). Short term exposure of tumor cells to bryostatin induces PKC activation with translocation of PKC to the membrane, whereas as prolonged exposure of tumor cells to bryostatin induces PKC's inhibition by causing its depletion from the cell. It has been reported that treatment of U937 human monoblastoid leukemic cells with bryostatin for less than 48 hours resulted in the inhibition of cdk2 activity with the dephosphorylation of threonine-160; whereas treatment of these cells with bryostatin for 72 hours or longer induced an increase in cdk2 activity with increased phosphorylation (36). Thus, these two studies support a hypothesis that, in terms of cell cycle mediated events, apoptosis induced by PKC inhibition is associated with an increase in cdk2 activity. It remains unknown whether this is secondary to decreased expression of cyclin inhibitors (i.e p21) that ordinarily bind to and inhibit cdk2 or whether it is a direct result of modification of the sites of cdk2 phosphorylation. The end results of these events would be to increase cdk2 activity.

PRELIMINARY STUDIES

Figure 5:
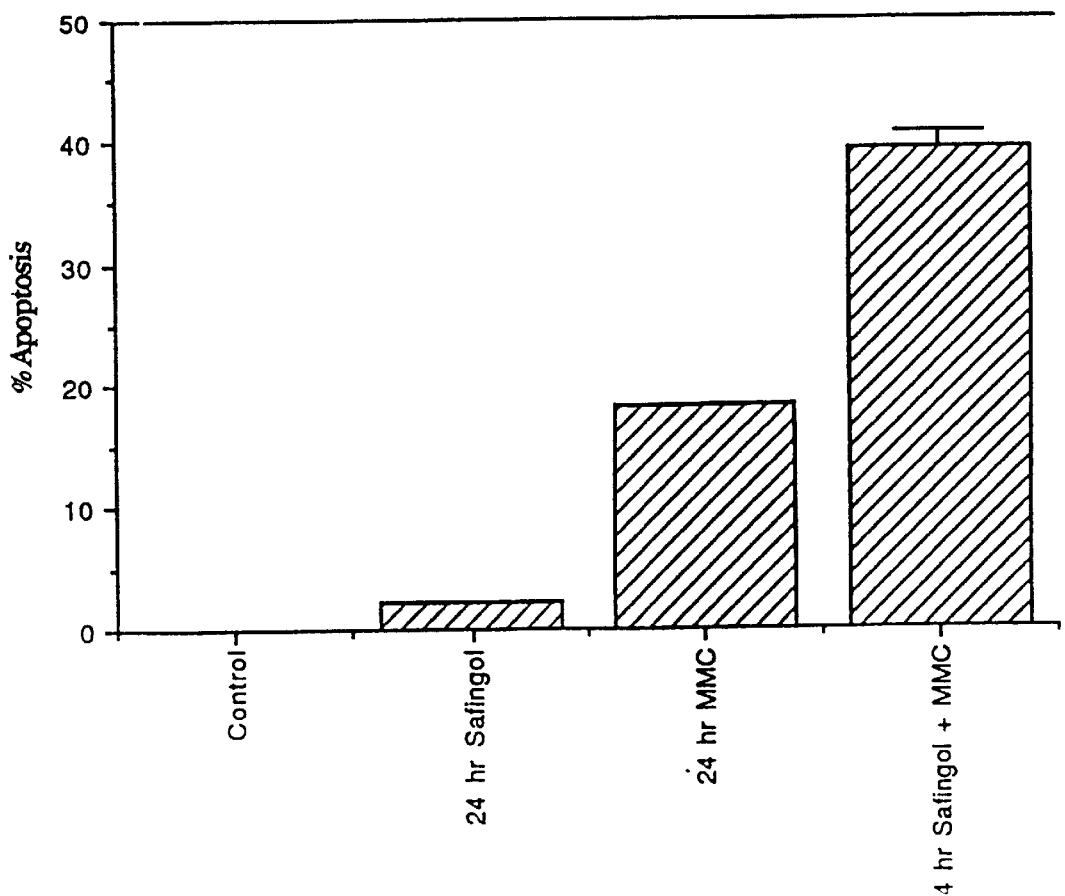
FIG. 5. Treatment with safingol alone did not induce significant levels of apoptosis (2%±1) when compared with untreated controls (<1%).

In vitro studies indicate that safingol, UCN-01, flavopiridol, and RO 32-0432 enhance MMC-induced apoptosis in gastric cancer cells:

(i) Safingol enhances MMC-induced apoptosis: SK-GT-5 cells, which have a mutated p53 gene (9), were treated with safingol in the presence or absence of MMC for 24 hours. For determination of apoptosis SK-GT-5 cells were treated according to one of several conditions: (i) no drug (control) for 24 hours, (ii) Safingol alone (50 $\mu$M) for 24 hours. (This concentration represents the highest non-toxic dose of safingol for the SK-GT-5 cells, as determined by cell proliferation studies, and slightly exceeds the safingol concentration (30 µM) which inhibits PKC enzyme activity by 50% in vitro.), (iii) Mitomycin-C alone (2.5 µg/ml) for 24 hours, (iv) Mitomycin-C alone (5 µg/ml) for 24 hours, (v) the combination of safingol (50 µM) and Mitomycin-C (2.5 µg/ml) for 24 hours, (vi) the combination of safingol (50 µM) and Mitomycin-C (5 µg/ml) for 24 hours. Apoptosis was measured by quantitative fluorescent microscopy (QFM) of nuclear changes induced by apoptosis, as determined by bisbenzimide trihydrochloride (Hoescht-33258) staining of condensed nuclear chromatin (3,5). For the QFM duplicate samples of 500 cells each were counted and scored for the incidence of apoptotic chromatin condensation using an Olympus BH-2 fluorescence microscope. As shown in FIG. 5, treatment with safingol alone did not induce significant levels of apoptosis (2%±1) when compared with untreated controls (<1%):

However, the combination of safingol and MMC significantly increased the percentage of cells undergoing apoptosis from 18%±1 with MMC alone to 39%±1% with the drug combination (p<0.001). MKN-74 cells, which are wild-type for p53, were subjected to the same treatments. Cell counts of MKN-74 cells following treatment with safingol alone indicated no significant induction of apoptosis (8%±3%) when compared to untreated controls (<1%). However, the combination of safingol and MMC significantly increased the percentage of cells undergoing apoptosis from 40%±4% with MMC alone to 83%±4% with safingol and MMC together (p<0.005).

Figure 6:
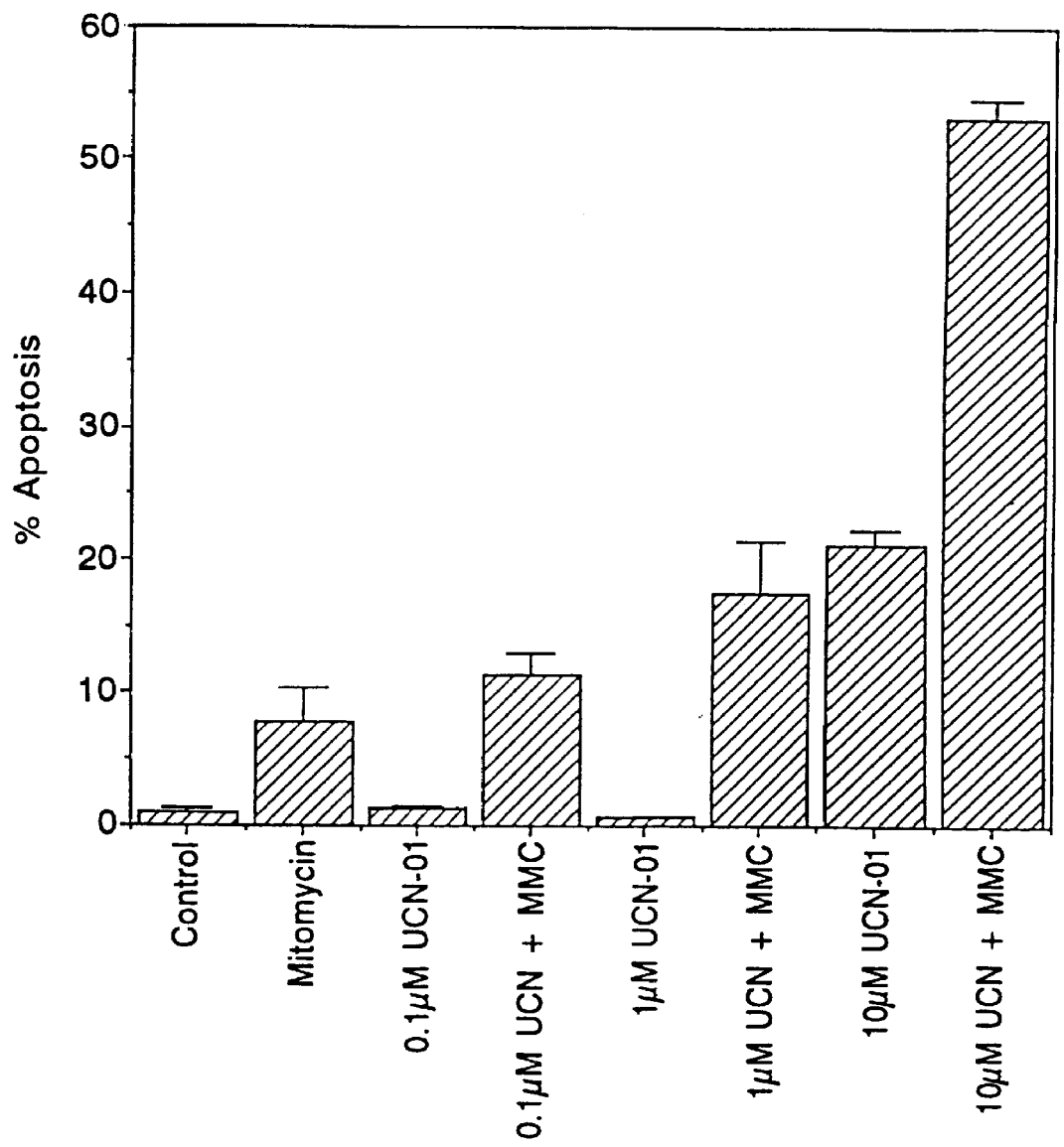
FIG. 6. UCN-01 enhances MMC-induced apoptosis: SK-GT-2 cells, which have a mutation in p53, were treated with increasing concentrations of UCN-01 in the presence or absence of a fixed dose of MMC for 24 hours. The results for the QFM analysis are shown in FIG. 6.

(ii) UCN-01 enhances MMC-induced apoptosis: SK-GT-2 cells, which have a mutation in p53, were treated with increasing concentrations of UCN-01 in the presence or absence of a fixed dose of MMC for 24 hours. The results for the QFM analysis are shown in FIG. 6.

MMC alone at the concentration 5.0 µg/ml induced apoptosis in 7%±3% of the SK-GT-2 cells. However, the combination of UCN-01 and MMC significantly increased the percentage of cells undergoing apoptosis in a dose-dependent. With 0.1 µM UCN-01 the percentage of gastric cancer cells undergoing apoptosis increased from 1%±0% with UCN-01 alone to 11%±2% with MMC and UCN-01 in combination. With 1 µM UCN-01, the induction of apoptosis increased from 1%±0 with UCN-01 alone to 18%±4% with the combination (p<0.01), and with 10 µM UCN-01 the induction of apoptosis increased from 21%±1% with UCN-01 alone to 53%±1% with the combination therapy (p<0.001). Applicants have observed comparable effects with the combination of UCN-01 and MMC against the breast cancer cell line MDA-MB-468 which has a mutation in the p53 gene (data not shown).

(iii) Flavopiridol inhibits PKC in nanomolar concentrations and enhances MMC-induced apoptosis: Flavopiridol is currently in phase I clinical trial at the NCI. In micromolar concentrations flavopiridol has been reported to inhibit PKC activity, but in nanomolar concentrations it has been reported to inhibit tyrosine kinases (24). Before testing flavopiridol's effect on enhancing MMC-induced apoptosis in applicants' cell system, applicants first elected to determine the extent to which flavopiridol inhibited PKC activity with PKC obtained from MKN-74 gastric cancer cells. For these experiments MKN-74 cells were homogenized and PKC was purified on a DEAE cellulose column as described (37). The PKC activity was determined by determining the extent to which the purified PKC phosphorylated myelin basic protein in the presence or absence of flavopiridol at 34 and 380 nM. A control sample was also run with the PKC pseudosubstrate, which functions as an established PKC inhibitor. The results, as shown in the table below, are expressed as the absolute counts of [$^{32}$P]ATP incorporated into myelin basic protein/minute of assay time:

| Condition | PKC activity | Percent inhibition |
|---|---|---|
| No drug | 25,000 | — |
| Flavopiridol (34 nM) | 4,000 | 84% |
| Flavopiridol (340 nM) | 3,300 | 87% |
| Pseudosubstrate (positive control) | 6,000 | 76% |

Figure 7:
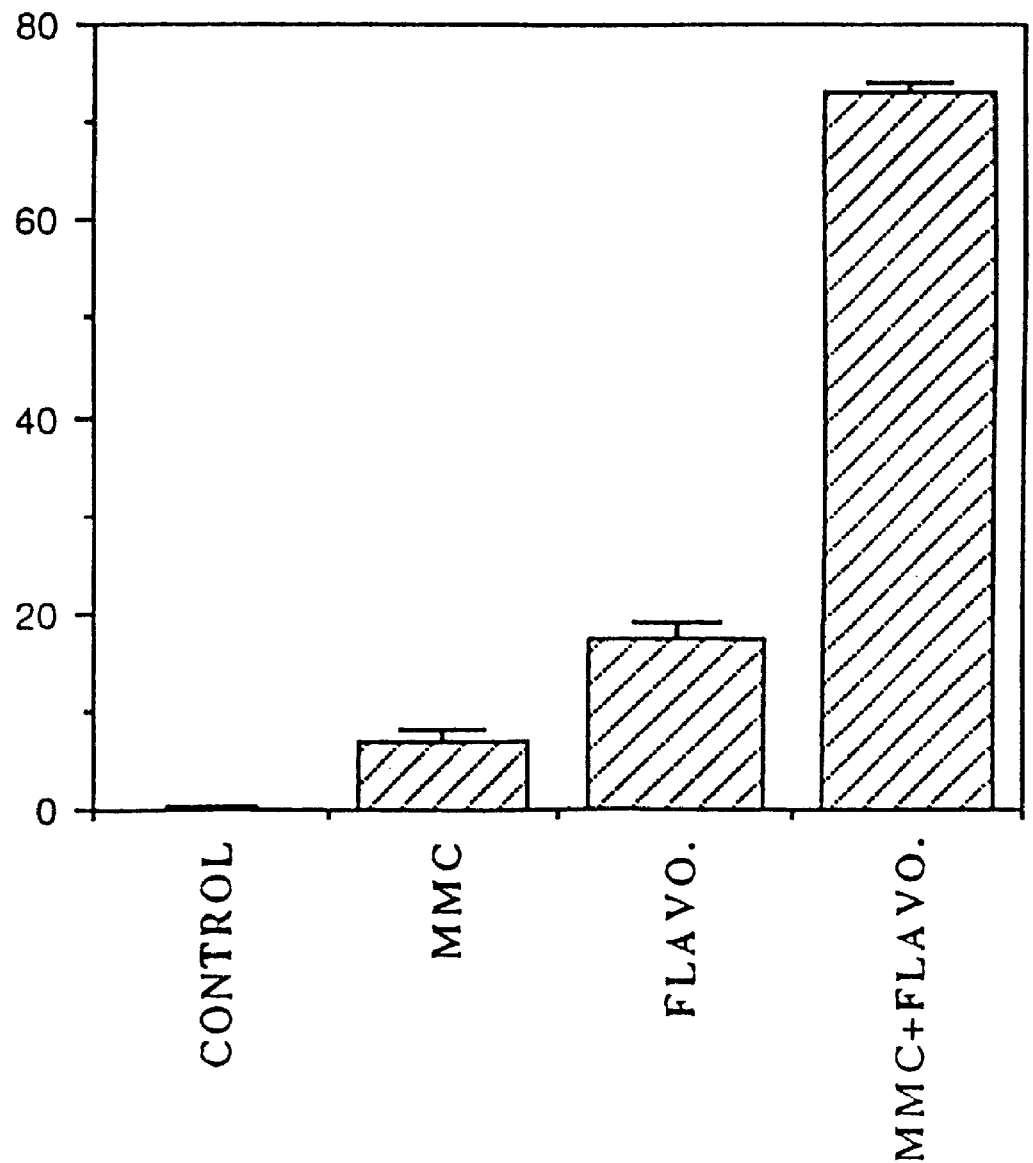
FIG. 7. Apoptosis was again measured by QFM staining. Applicants' results are shown in FIG. 7.

These results indicate that, in terms of the PKC obtained from MKN-74 cells, flavoperidol is an excellent PKC inhibitor. For this reason applicants next elected to test the effect of flavopiridol on enhancing MMC-induced apoptosis. For these studies the conditions were essentially the same as described above for safingol and MMC except that flavopiridol was used at a concentration of 300 nM and MMC remained fixed at a concentration of 50 µM. Apoptosis was again measured by QFM staining. The results are shown in FIG. 7.

Applicants' studies indicate that flavopiridol increased the induction of apoptosis from 7%±1% with MMC alone to 73%±1% with MMC and flavopiridol in combination. Flavopiridol alone induced a slight degree of apoptosis (17%±2%), but not nearly to the degree observed with the combination therapy.

(iv) RO32-0432 enhances MMC-induced apoptosis: Roche Pharmaceuticals has supplied us with several new PKC inhibitors to test for the enhancement of chemotherapy induced apoptosis. RO 32-0432 is one of series of bisindolylmaleimide inhibitors of PKC which are more selective than staurosporine (22). By introduction of a cationic sidechain and with conformational restriction of the amine sidechain, they have developed agents that are both highly PKC specific as well as orally bioavailable. For determination of apoptosis MKN-74 cells were treated according to the same conditions described for safingol and MMC except that RO32-0432 (1 µM) was substituted for safingol. Apoptosis was again measured by QFM (24). The combination of MMC with RO 32-0432 increased the percentage of cells undergoing apoptosis from 16%±2% with MMC alone to 25%±3% with 1 nM RO 32-0432 and to 41%±1% with 1 µM RO 32-0432. Similar to what applicants observed with the other PKC inhibitors, RO 32-0432 as a single agent had essentially no effect on inducing apoptosis of these cells.

(v) The combination of safingol and UCN-01 enhances MMC-induced apoptosis to a greater degree than either agent alone with MMC: Since both UCN-01 and safingol inhibit PKC by binding to two different sites of the enzyme, applicants tested the effect that these agents had together on enhancing MMC induced apoptosis of gastric cancer cells. For determination of apoptosis MKN-74 cells were treated according to one of several conditions: (i) no drug (control) for 24 hours, (ii) Safingol alone (50 µM) for 24 hours, (iii) UCN-01 alone (10 µM) for 24 hours, (iv) Mitomycin-C (MMC) alone (5.0 µg/ml) for 24 hours, (v) the combination of safingol (50 µM) and UCN-01 (10 µM) for 24 hours, (vi) the combination of safingol (50 µM) and Mitomycin-C (5 µg/ml) for 24 hours, (vii) the combination of UCN-01 (10 µM) and Mitomycin-C (5 µg/ml) for 24 hours, (viii) the combination of safingol (50 µM), UCN-01 (10 µM) and Mitomycin-C (5 µg/ml) for 24 hours. Apoptosis was again measured by QFM staining. The induction of apoptosis in the MKN-74 cells increased from 26%±5% with MMC alone, to 36%±1% with safingol and MMC, to 60%±2% with safingol, UCN-01, and MMC in combination. The induction of apoptosis by UCN-01 and MMC together for these cells was essentially no different than MMC alone. Thus the combination of UCN-01, safingol, and MMC induced a greater degree of apoptosis than any other condition tested in these sets of experiments.

Taken together (i-v) these results indicate that even though the PKC inhibitors safingol, UCN-01, and RO32-0432 can by themselves induce a slight degree of apoptosis in the breast and gastric cancer cells the induction of apoptosis is greatly enhanced when the PKC inhibitors are given in combination with MMC. The demonstration that these agents potentiate chemotherapy induced apoptosis may have important clinical implications in view of the recent introduction of at least two of these agents into clinical trials. Furthermore indications that the effect of combination of the two inhibitors on enhancing MMC induced apoptosis is greater than either PKC inhibitor alone with MMC would suggest another new direction for clinical development. Of particular importance is the finding that these agents are effective even with tumor cells that have a mutation in p53. Hence, the use of PKC inhibitors may provide a new approach to overcoming drug resistance in tumor cells that are resistant to chemotherapy because they lack p53 function. The purpose of these studies is then to determine how to optimize this effect in breast and gastric cancer cells by examining the best combinations of PKC inhibitors with chemotherapy as well as to examine the cellular basis of this phenomenon.

Safingol increases cells in S and in combination with chemotherapy increases cdk2 activity.

(i) Safingol effects the cell cycle by increasing the percent distribution of cells in S phase: applicants' studies indicate that safingol enhances chemotherapy induced apoptosis of gastric cancer cells in all phases of the cell cycle. However, since other PKC inhibitors, including UCN-01, have been shown to have cell cycle specific activity, despite the induction of apoptosis throughout the cell cycle, applicants elected to determine whether safingol also effected cell cycle specific events. In order to do this applicants first performed flow cytometry studies on MKN-74 cells synchronized in $G_2/M$ with nocodazole and then treated with safingol. Applicants believed that if these studies showed a perturbation in one particular phase of the cell cycle, then applicants could focus on a cell cycle event (e.g. cdk2) associated with a particular cell cycle phase (e.g. $G_1/S$). As shown in the table below, the cells were treated according to a series of different steps (noted as a "+" in the table) resulting in a series of different conditions (listed as A–E). The cells were analyzed for their percent distribution within the cell cycle as determined by flow cytometry:

As shown above, exposure of the cells to nocodazole (0.2 μg/ml) for 18 hours increased the cells remaining in $G_2/M$ from 9.8% in untreated controls (A) to 80% with the nocodazole therapy (B), consistent with a cell cycle block. When cells were washed free of nocodazole for 4 hours and then examined at that time point by flow cytometry, the percentage of cells in $G_2/M$ had decreased from 80% to 44.8% (indicating removal of the block), the percentage of cells in $G_1$ had increased from 7.7% to 33.2% and the percentage of cells in S phase had increased from 12.1% to 22.0% (C). However, if after washing out the nocodazole for four hours the cells were treated with 50 μM safingol (SAF) for an additional 24 hours, percentage of cells in S increased to 42.9% (D). This is in contrast to the cells treated with no drug during this additional 24 period. Under this condition the percentage of cells in S remained at 22.0%, suggesting that safingol induced an increase in the S phase fraction. In order to determine whether safingol was inducing an arrest of cells in $G_1/S$ the cells were treated according to these same conditions except that for the additional 24 hour period following the initial nocodazole washout, the cells were exposed to both safingol and nocodazole. Applicants anticipated that if the percent increase in S phase induced by safingol was due to cell cycle arrest then co-exposure with nocodazole would induce the cells to remain in S and not proceed into a $G_2/M$ block. As the results show (E), reexposure of the cells to nocodazole in the presence of safingol for the additional 24 hour interval resulted in an increase in the percentage of cells in $G_2/M$ from 19.9% with safingol alone to 65.5% with safingol and nocodazole and a decrease in the percentage of cells in S phase from 42.9% with safingol alone to 7.1% with safingol and nocodazole.

These results suggest that safingol does not induce a cell cycle arrest at $G_1$ or S but may be affecting a regulatory event within the cell cycle that promotes the induction of apoptosis once they pass through $G_1$ and enter S. Applicants proposed that a potential candidate for this regulatory event was cdk2.

(ii) Safingol increases cdk2 activity only when co-administered with chemotherapy: For determination of cdk2 activity MKN-74 cells were treated according to the conditions shown to enhance chemotherapy induced apoptosis: (i) no drug (control) for 24 hours, (ii) Mitomycin-C alone (5.0 μg/ml) for 24 hours, (iii) Safingol alone (50 μM) for 24 hours, (iv) the combination of safingol (50 μM) and Mitomycin-C (MMC, 5.0 μg/ml) for 24 hours. Cdk2 activity was determined by histone type-I phosphorylation, as described (38). For these studies cdk2 was first immunoprecipitated from the cell lysates following treatment under these four conditions. The kinase reaction was allowed to proceed at 30° for 30 minutes in the presence of histone type-I and [$^{32}$P]ATP. For each sample a control sample was run under the same conditions, but IgG was used in place of histone Type-I. This allowed for detection on non-specific kinase activity which was then subtracted out from the cdk2

| Condition | Nocodazole (18 hours) 0.2 μg/ml | Nocodazole Washout (4 hours) | Medium Alone (24 hrs) | SAF Alone, (24 hrs) 50 μM | SAF + Nocod. (24 hrs) | $G_1$ (%) | S (%) | $G_2/M$ (%) |
|---|---|---|---|---|---|---|---|---|
| A | − | − | − | − | − | 72.1 | 18.0 | 9.8 |
| B | + | − | − | − | − | 7.7 | 12.1 | 80.2 |
| C | + | + | + | − | − | 33.2 | 22.0 | 44.8 |
| D | + | + | − | + | − | 37.2 | 42.9 | 19.9 |
| E | + | + | − | − | + | 27.4 | 7.1 | 65.5 | activity to determine the absolute radioactive incorporation attributable to cdk2. The samples were transferred to a 10% SDS PAGE gel for analysis. The autoradiographs were analyzed on a phosphoimager for determinations of relative cdk2 activity. The results are shown in FIG. 8

Each lane represents the following: lane A, the IgG control; lane B, no drug therapy for 24 hours; lane C, MMC alone (5.0 µg/ml) for 24 hours; lane D, safingol alone (50 µM) for 24 hours; lane E, the combination of safingol (50 µM) and MMC (5.0 µg/ml) for 24 hours. The results indicate that untreated gastric cancer cells (lane B) have increased cdk2 activity and that both MMC (lane C) and safingol (lane D) have decreased cdk2. However, the combination of MMC and safingol increased cdk2 activity back to basal levels.

These results may explain why safingol, as a single agent, does not induce apoptosis, but for apoptosis to proceed in the presence of safingol there is an obligate requirement for concomitant exposure of the tumor cells to a chemotherapeutic agent (e.g.MMC). Applicants propose that apoptosis takes place when at least three conditions are met: DNA damage by chemotherapy, an increase in cdk2 activity, and inhibition of PKC activity. Thus, in control cells there is an increase in cdk2 activity but no DNA damage or PKC inhibition; in MMC treated cells there is DNA damage, a decrease in cdk2 activity, and no PKC inhibition (data not shown); and in safingol treated cells there is PKC inhibition but a decrease in cdk2 activity and no known DNA damage. However, with the combination therapy of safingol and MMC, all three conditions are met: increased cdk2 activity, DNA damage, and inhibition of PKC. Thus, apoptosis proceeds. The basis for the decrease in cdk2 activity by safingol (as well as by MMC) remains unknown and stands in contrast to the effects of UCN-01 and bryostatin as single agents. However, flavoperidol alone has been reported to inhibit the cdks (39), including cdk2 (Edward Sausville, NCI, Bethesda, Md.), at concentrations in which applicants have observed flavopiridol to inhibit PKC activity. All these results strongly suggest that cdk2 activity may be a major marker for the apoptosis associated with PKC inhibition. The increase in cdk2 activity with safingol and MMC, indicates a potential biomarker of apoptosis that will be tested in human tissues on applicants' clinical trials (see METHODS and PLANS below).

Safingol enhances the anti-tumor effect of cisplatin and doxorubicin in tumor-bearing animals Although safingol showed no direct anti-tumor activity in vivo, when tested as a single agent in a variety of murine tumor models and human tumor xenografts, its synergism with cisplatin and doxorubicin in vitro suggested it might potentiate the antitumor efficacy of these chemotherapeutic agents in vivo. For these experiments safingol was administered alone or in combination with cisplatin or DOX to female C3H/HeJ mice bearing 16C mammary carcinoma implanted intramuscularly. Antitumor response to the agents alone or in combination was assessed by tumor growth delay. Safingol by itself at doses of 5 to 20 mg/kg had no effect on inhibiting tumor cell growth. However, when administered intraperitoneally (i.p.) at a dose of 20 mg/kg and combined with intravenous (i.v.) cisplatin (10 mg/kg), safingol produced a modest enhancement in growth delay when compared to cisplatin alone. The administration of cisplatin under these conditions resulted in a the development of a 16/C mammary carcinoma that took 10 days to reach 5 times its starting size, whereas the combination of the same dose of cisplatin and a single dose resulted in a tumor mass that took 26 days to reach 5 times its starting size. Comparable effects against 16/C tumors were observed with safingol and DOX (10 mg/kg, i.v.) (74).

Safingol does not induce increased toxicity of chemotherapy in animals

From the preclinical data it appears that doses of safingol ranging from 10 to 20 mg/kg are necessary in order to achieve any level of chemopotentiation. Because safingol is being developed as a chemopotentiation agent, studies were conducted in rats and dogs to evaluate the ability of safingol to potentiate the toxicity of established cancer chemotherapeutic agents (40). Single-dose studies with rats in which safingol was administered prior to cisplatin, cyclophosphamide, or doxorubicin showed that safingol did not potentiate the myelotoxicity of these agents or affect reversal of the toxicity. No overt potentiation of cisplatin-mediated nephrotoxicity was observed. Cisplatin had no apparent effect on the pharmacokinetic profile of safingol. A possible effect of safingol on cisplatin pharmacokinetics was demonstrated by a statistically significant higher cisplatin Cmax value following safingol treatment, compared with the cisplatin Cmax value following vehicle administration. Other than the Cmax time point, the concentration-time profile of cisplatin was unaffected by safingol. A single-dose combination study in dogs indicated that safingol did not potentiate doxorubicin toxicity and vice versa, and that plasma concentrations of safingol or doxorubicin were also unaffected by administration of the other (Investigators brochure).

Intravenous administration of safingol in emulsion caused clinical pathology and histopathology findings consistent with venous irritation and transient intravascular hemolysis in mice, rats, and dogs (40). It seemed to occur as a function of safingol concentration and depended on the caliber of the vein used for delivery. Although venous irritation and hemolysis were significant and, in some instances, dose limiting toxicities in the animal studies, it was demonstrated that these effects may be mitigated by the use of low safingol concentrations and large-sized, high flow veins.

Results from the phase I clinical trial combining safingol with doxorubicin:

(i) Study design: This Phase I trial was designed as an open-label, non-randomized, dose escalation study, in which groups of three to six patients received on day 1 of each cycle received sequentially increased dosages of intravenous safingol emulsion and then (provided there was no acute toxicity) 14 days later received the same dose of safingol one hour prior to a fixed intravenous dose of doxorubicin. Individual patients could receive up to six cycles of treatment with the same dose of safingol and doxorubicin (DOX) every 21 days, until signs of tumor progression or unacceptable toxicity occurs, or until the patient's cumulative life-time dose of doxorubicin exceeds 400 mg/m$^2$ with an additional cycle of treatment. Prior DOX therapy was allowed up to a dose of 280 mg/m$^2$ as long as the left ventricular ejection fraction was >50%. The starting dose of safingol was 15 mg/m$^2$. This represented 1/10 the LD$_{10}$ in mice, 4% the highest non-toxic dose (HNTD) in dogs, and 12% the HNTD in rats.

(ii) Patient characteristics: To date applicants have entered 17 patients onto the study, all of whom are evaluable. The patient characteristic are as follows: 1) median age (range): 59 (29–77), 2) median KPS (range): 80 (70–90) 3) Male:Female : 10:7, 4) Primary sites of disease: pancreas:6, gastric:2, colon:3, unknown primary:2, sarcoma:3, nasopharyngeal:1;

(iii) No dose limiting hematologic Toxicity: As shown in the table below with a fixed doxorubicin dose of 45 mg/m² and escalating doses of safingol, there has been no-dose limiting hematologic toxicity. In fact the white blood count nadirs have increased with increasing safingol dose. Dose escalation above 120 mg/m² is planned.

Hematologic Toxicity with Safingol and DOX at 45 mg/m²

| Safingol (mg/m²) | # of patients | Mean White Blood Count (range) | Mean Absolute Neutrophil Count (range) | Mean Platelet Count (range) |
|---|---|---|---|---|
| 15 | 3 | 3.2 (1.4–5.0) | 1.2 (0.8–1.8) | 150 (121–189) |
| 30 | 4 | 4.6 (1.1–9.0) | 2.3 (0.4–4.0) | 187 (37–349) |
| 60 | 3 | 4.0 (2.2–6.1) | 2.3 (0.7–4.7) | 154 (70–233) |
| 120 | 3 | 5.4 (4.9–7.5) | 5.2 (2.3–5.1) | 283 (225–279) | b) No dose-limiting hemolysis: Thus far only one patient has experienced a grade I hemolysis as evidenced by a >50% decrease in serum haptoglobin. This was associated with no changes in reticulocyte count, no evidence of hemolysis on the peripheral smear, no "pink" discoloration to the plasma, and no evidence or urine hemosiderin. This was believed to be related to relatively poor venous access which only became apparent on the first day of therapy. The patient was retreated according to applicants' protocol criteria for grade I hemolysis which included infusion of safingol through a central vein and at one half the concentration (twice the total volume but the same total dose). Under these conditions the patient has experienced no further evidence of hemolysis.

(iii) Safingol pharmacokinetics appear linear with increasing dose: The pharmacokinetics of patients treated with safingol and DOX at 45 mg/m² is shown below:

Mean Plasma Safingol Pharmacokinetics with 45 mg/m² DOX

| Dose Level, mg/m² | Cmax, ng/ml | AUC. (ng × hr/mL) with DOX | AUC. (ng × hr/mL) without DOX |
|---|---|---|---|
| 15 (n = 3) | 199 | 168 | 161 |
| 30 (n = 4) | 336 | 501 | 428 |
| 60 (n = 3) | 422 | 531 | 501 |
| 120 (n = 3) | 988 | 1227 | 1226 |

It appears that with the safingol dose escalation the increases in plasma safingol levels is generally linear with increasing safingol dose. In addition, DOX did not change the pharmacokinetics of safingol.

Based on the mice studies applicants have predicted that in order to achieve meaningful chemopotentiation with either DOX or cisplatin applicants need to deliver the equivalent mouse dose of 5 mg/kg to 20 mg/kg saf ingol. From the preclinical pharmacology in the mice this translates into a Cmax and AUC of 1,797 ng/ml and 668 ng×hr/ml respectively for 5 mg/kg safingol and a Cmax and AUC of 7,021 ng/ml and 2,702 ng×hr/ml respectively for 20 mg/kg safingol. From the pharmacology data obtained thus far from the patients treated with escalating doses of safingol and 45 mg/m² of DOX, it appears that applicants are approaching these target levels. In view of this and the fact that applicants are still significantly below the predicted pharmacological toxicity levels, applicants continue to accrue patients to the study.

METHODS and PLAN

To develop an integrated clinical program with PKC inhibitors in combination with chemotherapy that uses laboratory correlates (PKC activity, cdk2 activity, and terminal deoxynucleotidyl transferase (TdT) activity in tumor tissues and leukocytes) as putative surrogate end-points of activity. The immediate goal will be to complete two current phase I clinical trials with the PKC specific inhibitor L-threo-dihydrosphingosine (safingol) in combination with (i) doxorubicin (DOX) and (ii) cisplatin with the plan to take this to a phase II study in gastric cancer; and to (iii) initiate additional clinical trials with combinations of chemotherapy and other PKC inhibitors including UCN-01, flavopiridol, and bryostatin.

Applicants now have two open MSKCC IRB-approved phase I studies with safingol. The first combination study with doxorubicin (see PRELIMINARY RESULTS) will close once applicants reach the MTD. Based on the pre-clinical data in gastric cancer cells a phase II study of safingol and doxorubicin will then be planned. In the interim the second study with safingol and cisplatin is soon to open. This study has been approved for funding as an administrative supplement by the NCI to the MSKCC P30 CA 08748-30. The study design and plan are as follows:

(i) To complete the phase I trial of safingol and doxorubicin.

(ii) To initiate a phase I study of safingol and cisplatin:

Study design: This Phase I trial is designed as an open-label, non-randomized, dose escalation study, in which groups of three to six patients will receive sequentially increased dosages of intravenous safingol emulsion, one hour prior to a fixed, 75 mg/m² intravenous dose of cisplatin, until dose limiting toxicity is demonstrated in at least three of six patients. Based on the current phase I study of safingol and doxorubicin, the starting dose for safingol in this new combination trial with cisplatin will be 60 mg/m². The dose of safingol will be fixed within each co-hort. Individual patients will receive additional cycles of treatment with the same dose of safingol and cisplatin every 21 days, until signs of tumor progression or unacceptable toxicity occurs.

iii) To initiate additional clinical trials with other PKC inhibitors including UCN-01, flavopiridol, and bryostatin.

a) A combination study of UCN-01 and Carboplatin: Based on applicants' pre-clinical data with UCN-01 as a PKC inhibitor that enhances the induction of chemotherapy induced apoptosis. The proposal for this study is that UCN-01 will be given on day 1 as a 24 hour infusion and carboplatin be given as 300 mg/m² bolus six hours after initiating UCN-01. UCN-01 will be escalated in subsequent co-horts but the dose of carboplatin will remain fixed. This treatment will be repeated every 28 days.

b) Future combination trials of PKC inhibitors (i.e bryostatin) and chemotherapy: For the future studies utilizing PKC inhibitors in combination with chemotherapy, applicants will use a general approach, as outlined below, to their development and conduct. These points, including biostatistical considerations, are also applicable to all the PKC inhibitory studies now in progress or proposed.

Patient eligibility and verification of eligibility: Patients will be selected from applicants' Department of Medicine populations. For general Phase I studies, all types of cancer will be included including gastric cancer, other gastrointestinal cancer, non-small cell lung cancer, refractory breast cancer, renal cell cancer, melanoma, gynecologic neoplasms, and sarcomas. This type of design allows us to do Phase I testing of highly specific new agents and utilizes the great depth of the MSKCC patient population. Memorial Sloan-Kettering Cancer Center has filed form HHS 441 (Re: Civil Rights), form HHS 641 (Re: Handicapped individuals) and form 639A (re: sex discrimination). In selecting patients for study in the proposed contract work, due notice is taken of the NIH/ADAMHA Policy concerning women and minorities in clinical research populations. The study population will be fully representative of the whole range of patients seen at Memorial Hospital. Unless a disease is gender specific, no eligibility limitations will be employed regarding age, gender, childbearing potential, race or ethnic origin.

Applicants' past record indicates a commitment to entering patients relatively early in the course of basically incurable advanced neoplasms (e.g., colorectal, renal cells, non small cell lung cancer). As no systemic therapy offers substantial benefit for such patients, applicants feel that Phase I therapy—especially studies to evaluate combinations seeking to enhance the activity of active drugs (e.g., MMC and Carboplatin) is the best therapy for many patients with these diseases. Measurable or evaluable tumor masses or parameters, while desirable, will not be required for eligibility.

Protocol Design: All Phase I PKC studies will be performed within the context of a specific written protocol. Each individual protocol will be initially designed after receipt of complete preclinical efficacy, toxicologic and pharmacologic information and discussions with NCI staff. A biostatistician (Ying Huang, Ph.D) is a member of the PKC Phase I Group and provides statistical methodology when it is necessary to deviate from the standard dose escalations. Particular attention will be given to blending applicants' Center's expertise with the needs of the NCI Phase I program. Applicants envision continued efforts toward developing combination therapy programs designed to modulate cytotoxicity and overcome resistance, using PKC as a novel drug target.

Initial Drug Dosage: In combined Phase I trials initial dose schedules will utilize known pharmacologic data on each drug, prior clinical experience using each drug individually (if available) and the biochemical rational for combining the drugs. Whenever possible, basic laboratory data will be used to determine sequence, schedule, modes of administration, target plasma levels, etc. However, applicants remain cognizant that modulating agents may not only alter the duration and intensity of the toxic effects of the anticancer agent they are paired with but the modulating agents themselves may have toxicities which must be taken into account in the phase I design.

Dose Escalation: The scheme of dose escalation is a key feature of Phase I trials. Historically, a traditionally empiric dose escalation has been employed with 3 patients in each dose cohort. For such empiric designs at MSKCC, the following scheme will be utilized: N, 2N, 4N, 8N; then escalation by increments of 30%. If any toxicity>grade 2 (except nausea and vomiting>grade 3) is seen early in the escalation, 30% increments of drug escalation will be begun from that level causing>grade 2 toxicity. Studies which combine modulators with chemotherapy must be designed differently than traditional Phase I studies. The design of these trials depends heavily on the support of laboratory investigators to establish target of modulation and to monitor the effects. For modulating agents, the goal is to administer the minimum dose of modulator which consistently results in the desired modulatory effects. In general, for the PKC inhibitor being escalated, applicants will choose a starting dose which is known to be without toxicity in previous human experience and will escalate from this dose in a conservative manner while maintaining the dose of the other agents constant.

Pharmacokinetics: Whenever possible, pharmacokinetics will be performed on both the modulator and the chemotherapeutic agent to establish the appropriate schedules for optimal combination. The biological endpoint must be ascertained for each patient to establish the appropriate modulator dose. Then, the chemotherapy dose must be escalated to identify the alterations in toxicity. In parallel, pharmacokinetics of both agents must be monitored to insure that drug-drug interactions do not materially alter the pharmacokinetic behavior of the two agents. Careful attention will be paid to the biostatistical design and analysis of the trial in order to discriminate the effects of each of the individual agents from those related to drug-drug interaction. Applicants believe that it is important to incorporate pharmacokinetic studies into applicants' Phase I trials. Applicants will perform pharmacokinetic analysis on 2–3 patients at the first level of a trial and at each subsequent level (assuming that the drug is detectable at the early levels). If the mouse pharmacokinetics are known (i.e., mouse $LD_{10}$ AUC) and if the pharmacokinetics of the drug can be considered linear, then a prediction of the "target" AUC at the human MTD can be made based on the mouse AUC, and the escalations necessary to reach the projected MTD can be assessed. Continued pharmacokinetic analysis during the course of the trial will allow us to monitor progress toward the MTD and allow us to carefully monitor the levels near the projected MTD. If applicants find that the MTD estimated by the AUC analysis will occur before level 4, applicants can amend applicants' protocol to approach the projected MTD more slowly, escalating by increments of 30%.

Biostatistical considerations: At least 3 study drug-naive patients at each level shall be necessary to fully evaluate that dose level. When a dose level with any patient experiencing Grade 3 or greater drug-related toxicity has been identified, at least 6 patients at that dose level will be required to more fully evaluate the nature of that toxicity. The MTD will be defined as that dose which produces reversible$\geq$grade 3 toxicity, exclusive of nausea and vomiting, in 2/6 patients treated.

The probability of dose escalation based on the true incidence of dose limiting toxicity at a specific dose level is shown in the table below.

True Toxicity risk 0.10 0.20 0.30 0.40 0.50 0.60

Probability of Escalation 0.91 0.71 0.49 0.31 0.17 0.08

Thus, the risk of escalation in high toxicity risk dose levels is less than 50% for true toxicity rates below 0.30.

One of the principal objectives of Phase I studies will be determination of the maximum tolerated dose schedule. As outlined above, the treatment dose will be increased after three patients have been treated at a given dose with no toxicity and further testing will take place at doses with toxicity seen in the first three patients. Because of the iterative nature of the process to determine MTD, the confidence limit around the true toxicity rate will be based on additional patients tested at the MTD. The following table gives the 90% confidence limits for the true toxicity rate as a function of the number of additional patients treated at the MTD and the number that experience toxicity.

| # Additional Patients at the dose | \# with Toxicity, | | | | | | |
|---|---|---|---|---|---|---|---|
| | 0 | 1 | 2 | 3 | 4 | 5 | 6 |
| 6 | .30 | .58 | .73 | .85 | .93 | .99 | |
| | 0 | .009 | .06 | .15 | .27 | .42 | |
| 8 | .31 | .47 | .60 | .71 | .81 | .89 | .95 |
| | 0 | .006 | .05 | .11 | .19 | .29 | .40 |
| 10 | .26 | .39 | .51 | .61 | .70 | .78 | .85 |
| | 0 | .005 | .04 | .09 | .15 | .22 | .30 |
| 12 | .22 | .34 | .44 | .53 | .61 | .68 | .75 |
| | 0 | .004 | .03 | .07 | .12 | .18 | .24 |

Thus, if 10 patients are treated at the MTD, and if for instance 2 patients have toxicity, there is a 90% chance that the true toxicity rate is between 4 and 51%. It is anticipated that most studies will require the accumulation of data on approximately 20–30 adult patients.

(iii) To perform correlative laboratory studies: Studies from applicants' laboratory with safingol, as well as studies utilizing other PKC inhibitors, indicate that the critical event for enhancement of chemotherapy induced apoptosis by PKC inhibition takes place at the $G_1/S$ interphase and that this is associated with increased cdk2 activity. Therefore, applicants' plan is to measure cdk2 activity, PKC activity, and apoptosis by TdT on tumor tissues and leukocytes obtained from patients on the clinical trials. For these studies applicants will obtain serial tumor biopsies and peripheral lymphocytes from all patients on the studies at three time points: a baseline before therapy, following treatment with the PKC inhibitor alone, and following treatment with the PKC inhibitor and chemotherapy. Lymphocytes will be obtained from peripheral blood by density gradient centrifugation over Ficoll, as described (41). Tumor cells will be carefully dissected from the biopsies so as to avoid contamination with normal tissue. When available tumor cells will be obtained from ascitic fluid with passage through a 30 $\mu$m nylon mesh, as described (42).

Cdk2 assays: For cdk2 assays tissues and cells will be lysed in Lysis Buffer containing 0.1% Tween-20, PMSF (0.2 mM), aprotinin (10 $\mu$g/ml), and leupeptin (10 $\mu$g/ml). Immunoprecipitation will be performed with 200 $\mu$g of protein lysate for each kinase reaction (38). Following incubation for 1 hour on ice with the cdk2 antibody the mixture will be equilibrated with protein A-beads (20–25 $\mu$l per immunoprecipitate). This was then rocked for 45–60 minutes in the cold room. The beads will be washed with Lysis Buffer and Hepes-KOH Kinase Buffer containing 50 mM beta-glycerophosphate. The kinase reaction mixture will contain 0.2 $\mu$g of histone type-I, 300 $\mu$M ATP, the kinase buffer, and [$^{32}$P]ATP. For each sample a control sample will be run with the same reaction mixture, but IgG will be used in place of histone Type-I. This allows for detection on non-specific kinase activity which is then subtracted out from the cdk2 activity to determine the absolute radioactive incorporation attributable to cdk2 activity. Each reaction will be allowed to proceed at 30° for 30 minutes and then the samples will be transferred to a 10% SDS PAGE gel for analysis.

PKC assays: For these studies tissues and cells will be homogenized with gentle ultrasonication. PKC assays will be performed as described (37), but myelin basic protein will be used as a substrate. Briefly, PKC will be extracted from the gastric cancer cells as described (21,61) using a 20 mM Tris-HCL (pH 7.5) buffer containing 2 mM EDTA, 2 mM EGTA, 5 mM $\beta$-mercaptoethanol, 0.5 mM phenylmethylsulphonyl fluoride, 10 ug/ml leupeptin, and 0.25M sucrose. Cells or tissues will be homogenized with brief sonication. The cell homogenates will then centrifuged at 100,000×g for 1 hour at 4° C. The supernatant represents the cytosolic fraction and the pellet the membrane fractions. The pellet is resolubilized in the original Tris-HCl buffer. Both fractions are then assayed for PKC activity for 15 minutes at 25° C. by determining the transfer of $\gamma$-phosphate group of adenosine-5'-triphosphate to myelin basic protein (Gibco Laboratory) in a 50 mM Tris-HCl (pH 7.5) buffer containing 8 mM % L-$\alpha$-phosphatidylserine, 24 ug/ml PMA, and 12 mM calcium acetate. The reaction mixture is then transferred to Whatman P-81 paper for liquid scintillation counting.

TdT assays: Fresh tissue will be fixed in 10% neutral buffered formalin in a coplin jar for 10 minutes at room temperature and then fixed with ethanol acetatic acid. For paraffin-embedded tissues, samples will first be deparaffinized with ethanol and then protein digested with Proteinase K. For the TdT assays, the ApopTag Kit (Oncor, Gaithersburg, Md.) is used (5,43). This method employs a fluoresceinated antidigoxigenin antibody directed against nucleotides of digoxigenin-11-dUTP (d-dUTP) which are catalytically added to the 3-OH ends of fragmented DNA by TdT. Briefly, fixed sections are washed and fixed with 1% paraformaldehyde. The fixed cells are incubated in a reaction mixture containing TdT and d-dUTP for 30 minutes at 37° C. Stop/wash buffer is added, and the cells are resuspended in 100 $\mu$l of fluorescinated anti-digoxigenin antibody for 30 minutes at room temperature. The slides are then washed with 0.1% Triton X-100 before they examined with a Olympus BH-2 fluorescence microscope equipped with a BH2-DM2U2UV Dich. Mirror Cube filter (Olympus, Lake Success, N.Y.) and scored for fluorescence. For positive controls a cytospsin preparation on a silanized slide of human peripheral lymphocytes stimulated with 1 $\mu$M dexamethasone will be used. For negative controls sham staining will be performed substituting distilled water for TdT.

In order to exclude an effect from chemotherapy alone, this assays will be repeated in the final co-hort of patients one level below the MTD. Three patients will first be treated with chemothrapy (i,e cisplatin) alone for cycle 1, followed 28 days later by the combination of safingol and cisplatin for cycle 2. Three other patients will first be treated with the combination of safingol plus cisplatin for cycle 1, followed 28 days later by the cisplatin alone for cycle The cellular responses will be determined at each of these dosing visits. After completion of the proposed phase I study applicants will examine the results of these assays to see whether an association exists between a change in these biological assays and clinical response and/or toxicity in the patients treated. The Wilcoxon rank-sum test will be employed to compare responders to non-responders (or toxicity vs. no toxicity) in order to test the validity of any possible associations observed in this patient population.

To perform laboratory studies with human gastric, breast, and ovary cancer cells to: i) study a variety of new PKC inhibitors currently under pre-clinical development as inducers of apoptosis in combination with chemotherapy; ii) define the optimal conditions in which to combine safingol, UCN-01, flavoperidol, or bryostatin with chemotherapy in order to achieve the maximum induction of apoptosis for the purpose of clinical trial development; and iii) further examine in vitro cdk2 and to identify other related cell cycle dependent proteins associated with induction of apoptosis and the inhibition of PKC;

(i) To evaluate a variety of new PKC inhibitors in combination with chemotherapy to determine their effect on induction of apoptosis: Selective PKC inhibitors other than safingol and UCN-01 may induce even greater degrees of apoptosis when combined with chemotherapy against breast (MDA-MB-468), gastric (SK-GT and MKN-74) and ovarian (OVCAR) cancer cells. The other PKC inhibitors to be tested for the induction of apoptosis against the cell lines including a series of Roche inhibitors (to be supplied by Roche Pharmaceuticals, Nutley, N.J.), and bryostatin 1 (36), an agent that activates PKC with short exposure but inhibits PKC following prolonged drug exposure by inducing PKC degradation. Apoptosis will be quantitated by two methods: (1) QFM staining: This method involves staining with bisbenzimide trihydrochloride (Hoescht-33258) of condensed chromatin which characterizes the cells undergoing apoptosis (3,5) and (ii) terminal deoxynucleotidyl transferase (TdT) assay which labels the 3'-OH ends of DNA fragments in apoptotic cells (5,43).

For QFM determinations, the cells are fixed in 3% paraformaldehyde and incubated at room temperature for 10 minutes. The fixative is removed and the cells are washed with 1× PBS, resuspended in 20 $\mu$l 1× PBS containing only 8 $\mu$g/ml of bisbenzimide trihydrochloride (Hoechst #33258), and incubated at room temperature for 15 minutes. Aliquots of the cells (10 $\mu$l) are placed on glass slides coated with 3-amino-propyl-triethoxysilane, and duplicate samples of 500 cells each were counted and scored for the incidence of apoptotic chromatin condensation using an Olympus BH-2 fluorescence microscope equipped with a BH2-DM2U2UV Dich. Mirror Cube filter (Olympus, Lake Success, N.Y.).

For the TdT assays, the ApopTag Kit (Oncor, Gaithersburg, Md.) will be used. This method will essentially be identical to the one described above for tissue and lymphocyte samples from patients except that after washing with 0.1% Triton X-100 the cells will be counterstained with propidium iodide (PI) solution. Green (d-dUTP labeled DNA strand breaks) and red (PI staining for total DNA content) fluorescence of individual cells are measured on a FACScan flow cytometer (Becton Dickinson, San Jose, Calif.). The resulting bivariate plots enables the detection of apoptotic events within the cell cycle. The $R_1$ cursor is set using the control specimen to define normal levels of green fluorescence (i.e., basal levels of apoptosis). Cells with fluorescence above the $R_1$ cursor are considered apoptotic. The data from 10,000 cells are collected and analyzed using CellFit and LYSYS software (Becton Dickinson).

(ii) To define the optimal conditions in which to combine safingol, UCN-01, flavoperidol, and bryostatin with chemotherapy for future clinical development: Safingol, UCN-01, and flavoperidol are now in phase I clinical trials. Combining these agents with chemotherapeutic agents appears to be the best way to maximize the beneficial effects of these drugs as anti-cancer agents against breast cancer cells. However, the optimal way in which to achieve this end remains to be defined. Applicants plan to pursue this issue with a series of studies:

The optimal chemotherapeutic agent(s): The plan is to perform experiments with safingol and UCN-01 in combination with other conventional chemotherapeutic agents such as cis-platin, Taxol, 5-fluorouracil and doxorubicin in order to determine the extent to which these agents induce apoptosis with these other agents in the breast (MDA-MB-468), gastric (SK-GT and MKN-74) and ovarian (OVCAR) cells. The methods to quantitate apoptosis will be by QFM and TdT assays, as described above.

Combinations of PKC inhibitors: Since many of these inhibitors act at different sites of the enzyme (regulatory vs. catalytic), it may be possible to combine multiple PKC inhibitors together with chemotherapy in order to further enhance the induction of apoptosis. For example, as applicants have shown, the combination of UCN-01 and safingol with MMC at the conditions described above induce a greater degree of apoptosis than treatment either PKC inhibitor alone with MMC. Further studies combining flavoperidol with safingol or with UCN-01 are planned and apoptosis will be quantitated by the QFM and the TdT technique.

The optimal sequence and timing of the PKC inhibitors with the chemotherapeutic agent: The exact sequence and timing of the PKC inhibitor relative to chemotherapy exposure in breast cancer cell remains unknown. For these experiments applicants propose exposing the breast and gastric cancer cells to safingol (50 $\mu$M) for different time intervals (30 minutes, 1 hour, 3 hours, 6 hours, 18 hours, and 24 hours), washing the cells free of drug, and then exposing to MMC 5 $\mu$g/ml) for 24 hours. The relative induction of apoptosis will then be quantitated as above. Conversely, cells will first be exposed to safingol for 24 hours, but the MMC exposure will now be limited to different time intervals before being assayed for apoptosis.

(iii) To examine in vitro cdk2 and to identify other related cell cycle dependent proteins associated with the induction of apoptosis and the inhibition of PKC: The basis for the increase in cdk2 activity by safingol and MMC in combination remains unknown. It may be related to a decrease in the expression of a cdk2 inhibitor (i.e. p21) or it may be related to a modification of a phosphorylated site on cdk2 which results in its activation. A further understanding of this process may lead to new surrogate markers of activity. In order to examine this further applicants plan to examine: 1) protein expression of p21 and p27 with immunoblotting using an enhanced chemiluminescence system using specific antibodies (Santa Cruz Biotechnology, Inc. Santa Cruz, Calif.); 2) differences in protein phosphorylation of cdk2 with [$^{32}$P]orthophosphate cell labelling, as previously described, using a cdk2 specific antibody suitable for immunoprecipitating (36); and 3) correlative studies of cdk2 activity as measured by the histone H1 kinase assays (38). Control cells will be treated in the same way as described above except that standard media without drug will be used for all incubations.

To determine whether a specific PKC isoform may be a critical target for drug development in induction of apoptosis with chemotherapy by: (i) testing whether antisense for PKC$\alpha$ in combination with MMC has superior anti-tumor activity against human gastric cancer cells when compared to either agent alone or to a PKC missense with MMC; (ii) testing other PKC antisense against other PKC specific isoforms in combination with chemotherapy; (iii) studying in gastric cancer cells whether any of the PKC isoforms are being preferentially inhibited during the induction of apoptosis.

(i) Testing whether antisense for PKC$\alpha$ in combination with MMC has superior anti-tumor activity against human gastric cancer cells when compared to either agent alone or to a PKC missense with MMC: applicants' results indicate that PKC represents a novel target for enhancing the induction of apoptosis by chemotherapy. However, PKC is ubiquitous in both normal and malignant tissue. Even though safingol's specificity represents a considerable advance in the development of PKC inhibitors especially as they pertain to eventual clinical development, even further specificity would still provide theoretical advantages in drug development.

PKC comprises a multigene family, consisting of at least 13 distinct genes which have 4 large constant regions separated by 5 variable regions (18,44). A current concept is that the variable regions of these 13 PKC isoforms encode isozymes-specific properties (45). These 13 PKC isozymes can be grouped into three categories based on $Ca^{2+}$ requirements for activation and phorbol ester binding activity. PKC is also the major cellular receptor for tumor promoting phorbol esters which, as analogues of DAG, directly activate PKC (19). These isoforms are designated $\alpha$, $\beta 1$, $\beta 2$, $\gamma$, $\delta$, $\epsilon$, $\eta$, $\theta$, $\mu$, $\zeta$, $\lambda$, and $\tau$. The biological significance of PKC heterogeneity is unknown, but it is speculated that, since they show differential tissue expression, specific PKC isoforms will phosphorylate different substrates and mediate distinct and different biological responses in the cells in which they are expressed. The role of these different isoforms is essentially unknown. However, identifying the isoform(s) involved in apoptosis would provide a more specific target for drug therapy.

Recent data have implicated PKCα in apoptosis. Studies have shown that if PKCα is inactivated then apoptosis can proceed. Most attempts to develop isoforms specific PKC inhibitors have been unsuccessful. However, some inroads have been made with PKCα by testing of antisense oligonucleotides. A 20 mer has been developed by Isis Pharmaceuticals (Carlsbad, Calif. 92008) which specificly inhibits the expression of human PKCα without affecting the expression of other PKC isoforms. It has been shown to inhibit the growth of subcutaneously implanted human tumor xenografts (46). This inhibition was dose-dependent when administered intravenously (i.v.) or intraperitoneally (i.p.) between 0.06 and 6 mg/ml.

Applicants' results indicate that the best way to maximize the therapeutic benefits of PKC inhibitors is to combine them with chemotherapy. Applicants have previously reported that all the SK-GT cell lines express PKCα mRNA and protein (15,47). Therefore, these cell lines appear to be appropriate for the evaluation of a PKCα anti-sense. The goal of this study is to test the combination of the PKCα anti-sense in combination with MMC for the first time in an in vivo system. The PKC inhibitor for these studies will be a 20 mer PKCα antisense. The dose and schedule (10 mg/kg, daily, i.p.) of the anti-sense in the vivo study will be based on preclinical toxicology, which has been generated by ISIS pharmaceutical. The dose appears to be a safe and well-tolerated dose when administered both i.p. or i.v. to tumor bearing nude mice. The anti-sense easily dissolves in saline. Doses of 100 mg/kg have been given to mice on a daily schedule with no major toxicity and no deaths. At the highest non-toxic dose (100 mg/kg) mild lymphocytic infiltration has been noted in the liver, spleen and kidney. In order to determine the specificity of this response, a missense 20 mer will also be administered to two of the control groups. This will ensure that the observed response is secondary to the effect of the PKCα anti-sense and not due to a non-specific effect of the anti-sense therapy. The missense selected has also been safely administered at 10 mg/kg i.p to mice on a daily schedule without significant toxicity. The dose of MMC selected for these studies will be 14.5 mg/kg in saline. This dose has been safely administered to nude mice and has also been safely administered to nude mice when combined with the PKC inhibitor UCN-01 (31).

The animal protocol (MSKCC IACUC #95-07-027) design will be as follows: All animals with be injected subcutaneously into the hind quarter on day 1 with $5 \times 10^6$ SK-GT-2 cells. Applicants' preclinical; data indicates that within 10–12 days these animals develop a palpable 0.25 gr. tumor mass. Once the animals have a palpable tumor, they will be randomly assigned to one of 4 treatment arms (17 animals in each arm):

(1) PKCα anti-sense: by itself at a dose of 10 mg/kg/day i.p. daily for four weeks, (2) PKCα anti-sense+MMC: PKC anti-sense will be given at a dose of 10 mg/kg i.p daily for two weeks. On the first day of week #3 MMC will be given as a single i.v. dose (14.5 mg/kg). PKC anti-sense will be repeated i.p daily for an additional two weeks (i.e. weeks #3 and 4). (3) MMC alone: Daily i.p injections of a saline control for two weeks. On the first day of week #3 a single dose of Mitomycin-C well be administered (14.5 mg/kg) i.v.. This will be followed by two additional weeks of i.p. saline control. (4) PKCα missense: by itself at a dose of 10 mg/kg/day i.p. daily for four weeks.

Assuming a "non-treatment" response rate of 5% (i.e. antisense alone or Mitomycin-C alone) relative to the control animals (missense alone), then in order to detect a 50% decrease in size of the palpable tumor mass for the treated group (i.e antisense+Mitomycin-C) using a one sided alternative normal approximation z-test with a significance of 0.05 and a power of 80%, the total number of animals for each group needs to be 17. The total number of animals will be 64.

(ii) Testing other PKC antisense against other PKC specific isoforms in combination with chemotherapy: If antisense for PKCα does not show an enhancement of MMC-induced apoptosis, then anti-sense against the other PKC isoforms will be tested according to the same study design. The materials for these PKC specific anti-sense studies will be supplied by Isis Pharmaceuticals (Carlsbad, Calif.), as become available.

(iii) Studying in gastric cancer cells whether any of the PKC isoforms are being preferentially inhibited during the induction of apoptosis: Even though safingol is not PKC isoform specific, in regard to the induction of apoptosis safingol may still be inhibiting one isoform preferentially over another. One way to study this is to examine the relative distribution of the PKC isoforms between the membrane and the cytosolic fractions of the cells. PKC isoforms become activated when they are translocated from the cytosol to the membrane of the cell (48). Conversely, inactivation of these isoforms is associated with depletion of the isoform(s) from the membrane component of the cells. In order to test the influence of isoform distribution on chemotherapy induced apoptosis, applicants propose treating the cell lines with the four conditions that applicants have used in applicants' prior studies: (i) no drug (control) for 24 hours, (ii) Safingol alone (50 $\mu$M) for 24 hours, (iii) Mitomycin-C alone (5 $\mu$g/ml) for 24 hours, (iv) the combination of safingol (50 $\mu$M) and Mitomycin-C (5.0 $\mu$g/ml) for 24 hours. Since the distribution of the PKC isoforms between the cytosolic and membrane fraction of the cells appears to be the critical event for their relative activation, applicants will obtain cytosolic and membrane fractions, as described (13), to determine whether there are differences in isoform expression and localization with these different drug treatments that applicants have shown induce apoptosis. Briefly, PKC will be extracted from the gastric cancer cells, using a 20 mM Tris-HCL (pH 7.5) buffer containing 2 mM EDTA, 2 mM EGTA, 5 mM $\beta$-mercaptoethanol, 0.5 mM phenylmethylsulphonyl fluoride, 10 ug/ml leupeptin, and 0.25M sucrose (Buffer A). Cells will be homogenized and th homogenates will then be centrifuged at 100,000×g for 1 hour at 4° C. The supernatant represents the cytosolic fraction and the pellet which is resolubilized in buffer A containing 0.1% Triton-X represents the membrane fraction. These fractions are then passed through a DEAE-52 column and the PKC protein is eluted off the column with Buffer A containing 0.15M NaCl. Briefly, cells are lysed following drug treatment with lysis buffers containing protease and phosphatase inhibitors. Proteins are resolved by SDS-PAGE electrophoresis. Immunoblots are prepared with Immobilon P membranes by electrophoretic transfer and blocked in TN-Tween buffer (50 mM Tris, pH 7.5, 200 mM NaCl, 0.1% Tween-20) containing 5% (w/v) nonfat dry milk. After washing the blots are incubated with horseradish peroxidase-conjugated secondary antibodies (dilution 1/2000. Immunologically reactive protein will be visualized with the enhanced chemiluminescence system (Amersham, Arlington Heights, Ill.). using PKC isoform specific antibodies (49) (Santa Cruz Biotechnology, Inc. Santa Cruz, Calif.).

Reference of the Second Series Experiment

1. Lowe S. W., Ruley H. E., Jack T., Housman D. E. p53-Dependent apoptosis modulates the cytotoxicity of anticancer agents. Cell 74: 957–967, 1993.
2. Evans D. L. and Dive C. Effects of cisplatin on the induction of apoptosis in proliferating hepatoma cells and nonproliferating immature thymocytes. *Cancer Res.* 53: 2133–2139, 1993.
3. Haimovitz-Friedman A., Chu-Cheng K., Ehleiter D., Persaud R. S. et al. Ionizing radiation acts on cellular membranes to generate ceramide and initiate apoptosis. J. Exp. Med. 180: 525–535, 1994.
4. Jarvis W. D., Kolesnick R. N., Fornari F., Traylor R. S., Gewirtz D. A. and Grant S. Induction of apoptotic DNA damage and cell death by activation of the sphingomyelin pathway. Proc. Natl. Acad. Sci. U.S.A. 91:73–77, 1994.
5. Schwartz G. K., Haimovitz-Friedman A., Dhupar S. K., Ehleiter D., Maslak P., Loganzo F., Kelsen D. P., Fuks Z., Albino A. P. Potentiation of apoptosis by treatment with the protein kinase C specific inhibitor safingol in mitomycin-c treated gastric cancer cells. J. Natl. Cancer Institute 87(18): 1394–1399, 1995.
6. Jarvis W. D., Fornari F. A., Browning J. L., Gewirtz D. A., Kolesnick R. N., and Grant S. Attenuation of ceramide-induced apoptosis by diglyceride and pharmacological activators of protein kinase C in human myeloid leukemia cells. J. Biol. Chem. 268:31685–31692, 1994.
7. Jarvis W. D., Turner A. J., Povirk L. F., Traylor R. S., and Grant S. Induction of apoptotic DNA fragmentation and cell death in HL-60 human promyelocytic leukemia cells has been reported for pharmacological inhibitors of protein kinase C. Cancer Res. 54: 1707–1714, 1994.
8. Wingo P. A., Tong T., and Bolden S. Cancer Statistics, 1995. *CA* 45:19–36,1995.
9. Blot W. J., Devesa S. S., Kneller R. W., Fraumeni J. F., Jr. Rising incidence of adenocarcinoma of the esophagus and gastric cardia. *JAMA* 265:1287–91, 1991.
10. Kelsen D., Atiq O.Therapy of upper gastrointestinal tract cancers. *Curr. Probl. Cancer*:239–294, 1991.
11. Goldstein L. J., Galski H., Fojo A., Willingham M., Lai S. -L., Gazdar. Expression of a multidrug resistance in human cancers. *J. Natl. Cancer Inst.* 81:116–24, 1989.
12. Altorki N., Schwartz G. K., Blundell M., Davis D., Kelsen D, and Albino A. Characterization of cell lines established from human gastric-esophageal adenocarcinomas: Biologic phenotype and invasion potential. *Cancer* 72: 649–657, 1993
13. Schwartz G. K., Wang H., Lampin N., Altorki N., Kelsen D., Albino A. Defining the invasive phenotype of proximal gastric cancer cells. *Cancer,* 73: 22–27, 1994.
14. Nabeya Y., Loganzo F., Maslak P., Lai L., de Oliveira A., Schwartz G. K. et al. The mutational status of p53 protein in gastric and esophageal adenocarcinoma cell lines predicts sensitivity to chemotherapeutic agents. *Int.*
15. Schwartz G. K., Jiang J., Kelsen D., and Albino A. P. Protein kinase C: a novel target for inhibiting gastric cancer cell invasion. *J. Natl. Cancer Inst.* 85: 402–407, 1993.
16. Matozaki T., Sakamoto C., Matsuda K., Suzuki T., Konda Y., Nakono O et al. Mis-sense mutations and a deletion of the p53 gene in human gastric cancer. *Bioch. Bioohys,. Res. Comm* 182: 215–223, 1992.
17. Tamaoki, T. and Nakano, H. Potent and specific inhibitors of protein kinase C or microbial origin. *Biotech.,* 8: 732–735, 1990.
18. Kikkawa, U., Kishimoto, A., and Nishizuka, Y. The protein kinase C family: heterogeneity and its implications. *Annu.Rev. Biochem.,* 58: 31–44, 1989.
19. Bell, R. M., and Burns, D. J. Lipid activation of protein kinase C. *J.Biol. Chem.,* 266: 4661–4664, 1991.
20. Nakano, H., Kobayashi, E., Takahashi, I., Tamaoki, T., Kuzuu, Y., and Iba, H. Staurosporine inhibits tyrosine-specifid protein kinase activity of Rous sarcoma visus transforming protein. *J.Antibiot.* (Tokyo), 40: 706–708, 1987.
21. Takahashi I., Saitoh Y., Yoshida M., Sano H., et al. UCN-01 and UCN-02, new selective inhibitors of protein kinase C. *J. Antibiot.* 42: 571–576, 1989.
22. Birchall A. M., Bishop J., Bradshaw D., Cline A., Coffey J., Elliott L. H., et al. RO 32-0432, a selective and orally active inhibitor of protein kinase C prevents T-cell activation. *J. Pharmacol. Exp. Therapeutics* 26:922–929, 1994.
23. Kraft A. S., Smith J. B., and Berkow R. L. Bryostatin, an activator of calcium phospholipid-dependent protein kinase, blocks phorbol ester-induced differentiation of human promyelocytic HL-60 cells. *Proc. Natl. Acad. Sci. USA* 83:1334–1338,1986.
24. Kaur G., Stelter-Stevenson M., Sebers S., Worland P., Sedlack H., Myers C., Czech J., Naik R., Sausville E. Growth inhbition with reversible cell cycle arrest of carcinoma cells by flavone L86-8275. *J. Natl. Cancer Inst.* 84: 1736–1740, 1992.
25. Hannun, Y. A., Loomis, C. R., Merrill, A. H., Jr., and Bell, R. M. Sphingosine inhibition of protein kinase C activity and of phorbol dibutyrate binding in vitro and in human platelets. *J.Biol.Chem.,* 261: 12602–12609, 1986.
26. Adams L. M., Dykes D., Harrison S. D., Saleh J., and Saah L. Combined effect of the chemopotentiator SPC-100270, a pro tein kinase C inhibitor, and doxorubicin or cisplatin (Cis) on murine isografts and human tumor xenografts. *Proc. Amer. Assoc. Cancer Res.* 34:410, 1993.
27. Schwartz G. K., Ward D., Saltz L. Casper E., et al. A phase I study of the protein kinase C specific inhibitor safingol alone and in combination with doxorubicin. Proc. Amer. Soc. Clin. Onc. 14:1557,1995.
28. Sachs C. W., Safa A., and Fine R. L. Inhibition of protein kinase C by Safingol is associated with chemosensitization of multidrug resistant MCF-7 cells. Proc. Amer. Assoc. Cancer Res. 35:447, 1994.
29. Adams L. M., Cofield D. J., Seldin J. C., Kitchen P. A., et al. Effect of the protein kinase C (PKC) inhibitor SPC-100270 on drug accumulation and cytotoxicity in drug resistant and sensitive tumor cell in vitro. Proc. AACR 34:410, 1993.
30. Johnson M., Dimitrov D., Vojta P. J., Barrett J. C., Noda A., Pereira-Smith O, and Smith J. Evidence for a p53- independent pathway for upregulation of SDI1/CIP1/WAF1/p21 RNA in human cells. *Mol. Carcinogenesis* 11: 59–64, 1994.
31. Akinaga S., Nomura K., Gomi K., Okabe M. Enhancement of anti-tumor activity of mitomycin C in vitro and in vivo by UCN-01, a selective inhibitor of protein kinase C. *Cancer Chem Pharm* 32: 183–189, 1993).
32. Wang Q., Worland P. J., Clark J. L., Carlson B. A., Sausville E. A. Apoptosis in 7-hydroxystaurosproine-treated T lymphoblasts correlates with activation of cyclin-dependent kinases 1 and 2. *Cell Growth and Diff.* 6:927–936, 1995.
33. Gu Y., Rosenblatt J., and Morgan D. Cell cycle regulation of cdk2 activity by phosphoryaltion of Thr 160 and tyr15. *EMBO J.* 11: 3995–4005, 1992.
34. Shi L., Nishioka W. K., Th'ng J., Bradbury M., Litchfield, Greenburg A. H. Premature p34$^{cdc2}$ activation required for apoptosis. *Science* 263: 1143–1145, 1994.
35. Philip P. A., Rea D., Thavasu P., Carmichael J., Nicholas S. A., Rockett H., et al. Phase I study of bryostatin 1: Assessment of IL-6 and Tumor necross factor induction in vivo. *J. Natl. Cancer Instit.* 85: 1812–1818, 1993.
36. Asiedu C. Biggs J. Lilly M., Kraft A. S. Inhibition of leukemic cell growth by the protein kinase C activator bryostatin 1 correlates with the dephosphorylation of cyclin-dependent kinase 2. *Cancer Res.* 55: 3716–3720, 1995.
37. Schwartz G. K., Arkin H., Holland J. F. and Ohnuma T. Decreased protein kinase C activity and multidrug resistance in MOLT-3 human lymphoblastic leukemia cells resistant to trimetrexate. *Cancer Res.,* 51: 55–61, 1991.
38. Koff A., Cross F., Fisher A., Schumacher J., Leguelle K., Philippe M., and Roberts J. Human cyclin E, a new cyclin that interacts with two members of the cdc2 gene family. *Cell* 66: 1217–1228, 1991.
39. Losiewicz M. D., Carlson B. A., Kaur G., Sausville E. A., Worland P. Potent inhbition of cdc2 kinase activity by the flavonoid L86-8275. *Bichem Biophys. Res. Comm.* 201: 589–595, 1994.
40. Kedderis L. B., Weiler M. S., Christian B. J., Thomford P. J., Hall R. L., Salamon C. M., Harrison S. D., Jr., and Susick R. L. Preclinical safety assessment of SPC-100270 Emulsion, a novel protein kinase C inhibitor under development for use as a chemopotentiation agent. *Proc. Amer. Assoc. Cancer Res.,* 34:410, 1993.
41. Wakamiya N., Stone N., Takeyama H., Spriggs D., and Kufe D. Detection of tumor necrosis factor gene expression as a cellular level in human acute myeloid leukemia. *Leukemia* 3: 51–56, 1989.
42. Hirte H. W., Clark D. A., Mazurka J., O'Connell G., and Rusthoven J. A rapid and simple method for the purification of tumor cells from ascitic fluid of ovarian carcinoma. *Gynecologic Onc.* 44: 223–226, 1992.
43. Schmitz G., Walter T., Serbel R., and Kessle C. Nonradioactive labeling of oligonucleotides in vitro with the hapten digoxigenin by tailing with terminal transferase. *Anal. Biochem.* 192: 222–231, 1991.
44. Coussens, L., Parker, P. J., Rhee, L., Yang-Feng, T. L., Chen, E., Waterfield, M. D., Franke, U., and Ullrich, A. Multiple, distinct forms of bovine and human protein kinase C suggests diversity in cellular signaling pathways. *Science,* 233: 859–866, 1986.
45. Nishizuka, Y. Studies and perspectives of protein kinase C. *Science,* 233: 305–312, 1986.
46. Dean N. M.,, McKay R., Miraglia L., Marcel M., Fabbro D. Inhibition of growth of xenografted human tumor cell lines in the nude mice by an antisense oligonucleotide targeting human PKCα. *Proc. Amer. Assoc. Cancer Res.* 36: 413, 1995.
47. Schwartz G. K., Dhupar S. K., Nabeya Y., Kelsen D., Yokozaki H., Tahara E., and Albino A. P. Evidence that increased protein kinase C activity in metastatic gastric cancer cells is attributable to PKC isoforms other than PKCβ. *Proc. Amer. Assoc. Cancer Res.,* 35: 61, 1994.
48. Kraft A. S. and Anderswon W. B. Phorbol esters increase the amount of $Ca^{2+}$-phospholipid-dependent protein kinase associated with the plasma membrane. *Nature* 351: 621–623, 1983.
49. Blobe G. C., Sachs C. W., Khan W. A. Fabbro D., Selective regulation of expression of proteinkinase C (PKC) isoforms in multidrug resistant MCF-7 cells. *J. Biol. Chem.* 268: 658–664, 1993.

Third Series of Experiments
Protein Kinase C as a Novel Target for Inducing Apoptosis in Breast Cancer This invention develops new therapeutic approaches in the treatment of breast cancer by utilizing protein kinase C (PKC) as a target for inducing apoptosis in breast cancer cells. The specific aims are:

1. To determine the optimal chemotherapeutic agents to combine with the PKC specific inhibitors safingol and UCN-01 in the induction of apoptosis;
2. To evaluate other novel PKC inhibitors in combination with chemotherapy to determine their effects on induction of apoptosis;
3. To test the optimal combination and sequence of PKC inhibitors with chemotherapy;
4. To determine whether a specific PKC isoform may be a critical target for drug development in inducing apoptosis in breast cancer cells;
5. To assess the relationship between PKC and cell cycle regulation in the induction of apoptosis.

BACKGROUND and SIGNIFICANCE

In the United States adenocarcinoma of the breast is the most common malignant neoplasm in women. It is estimated that over 182,000 new cases of breast cancer will be diagnosed in 1995 and this will be associated with approximately 46,000 deaths, making breast cancer the second leading cause of cancer related-death in women in the United States (1). The incidence of breast cancer has been rising steadily in this country at a rate of one to two percent a year. Even though multi-agent chemotherapy in the adjuvant setting has had a significant impact on improving overall survival, the five year survival in node-positive breast cancer following adjuvant chemotherapy still remains approximately 65% (2). Furthermore, for metastatic breast cancer, despite innumerable clinical trials using various combinations of chemotherapy, the survival of patients has not significantly improved (3). Because of the high incidence of breast cancer worldwide, even small improvements in the efficacy of treatment may represent improved survival for tens of thousands of patients.

The breast tumors of many of these patients are resistant to the most active chemotherapeutic agents. The basis of drug resistance in breast cancer has not been well defined. The expression of the multi-drug resistant gene (mdr1) in breast cancer is low (4), suggesting alternate mechanisms of drug resistance. Recent studies have indicated a link between the induction of apoptosis (programmed cell death) and p53 expression (5). Cells which express wild-type p53 are capable of undergoing apoptosis after exposure to common chemotherapeutic agents or ionizing radiation; whereas cells with mutated or deleted p53 are resistant, avoiding apoptosis and continuing to replicate. Similarly, in breast cancer mutation in p53 has been associated with increased chemotherapy resistance (6). The incidence of p53 mutation in breast cancer has been reported to be 22% in primary lesions of patients with sporadic carcinomas (7) and may be as high as 50% in lymph nodes containing metastatic disease (8). For familial syndromes the incidence ranges from 34% for patients with familial breast cancer to 52% in patients with the familial breast and ovary cancer syndrome (7). In view of the prevalence of p53 mutations in breast cancer overcoming this form of resistance may greatly enhance the efficacy of cancer chemotherapy.

A large body of evidence indicates a fundamental role for protein kinase C (PKC), a multigene family of serine/threonine protein kinases, in processes relevant to neoplastic transformation, carcinogenesis, and tumor cell metastases (9–12). The activity of PKC has been reported to be increased in human breast cancer cell lines as (13), well as human breast cancer tissue as compared to normal breast tissue from the same patient (14). Consequently, PKC may represent a novel target for anti-cancer therapy in breast cancer. In order to test this hypothesis the PKC specific inhibitor safingol (e.g. the L-threo enantiomer of dihydrosphingosine) has been tested both by itself and in combination with conventional chemotherapeutic agents. While safingol as a single agent had negligible impact on tumor growth of mice-bearing mouse mammary 16/C and MT#7 carcinomas, the combination of safingol with doxorubicin or cisplatin substantially potentiated the anti-tumor effects of these drugs (15). Based on these observations, safingol, used in combination with doxorubicin, has become the first PKC specific inhibitor to enter clinical trials (16).

The mechanism by which safingol potentiates the activity of chemotherapeutic agents is unclear, although inhibition of P-glycoprotein phosphorylation and reversal of the multidrug resistant (mdr) phenotype in breast cancer cell lines has been suggested (17–18). While this hypothesis can explain the synergism achieved with combinations of safingol and doxorubicin, it does not explain the synergism reported for combinations of safingol with drugs that are not believed to produce resistance by the mdr mechanism (e.g., cisplatin) (15), nor does it explain safingol-induced effects that occur in tumor cell lines that do not express the P-glycoprotein (18). Therefore, pathways other than P-glycoprotein inhibition are likely to be involved in the safingol-mediated enhancement of chemotherapy.

It has been suggested that the anti-tumor activity of many chemotherapeutic agents (e.g., cisplatin and etoposide) is a consequence of their induction of apoptosis (5,19). In this context it has been proposed that activation of PKC acts as an antagonist to apoptosis, whereas inhibition of PKC promotes apoptosis (20–22). Thus, safingol-mediated potentiation of chemotherapy might be attributed to its PKC inhibitory effect, subsequently leading to increased apoptosis after drug-induced damage. In order to test this hypothesis applicants initially sought to determine the extent to which safingol by itself, or in combination with a specific chemotherapeutic drug (e.g. mitomycin-C, MMC), would promote apoptosis in gastric cancer cells. Furthermore, applicants investigated whether the p53 status of these cells influences the development of apoptosis after treatment with safingol and MMC (23).

For these initial studies applicants used the gastric cancer cell lines SK-GT-5 cells, which have a mutated p53 gene and are resistant to MMC, and MKN-74, which are wild-type for p53 and sensitive to MMC (23). Neither cell line expresses P-glycoprotein. Applicants' results show that safingol alone did not induce apoptosis in either the MMC-sensitive MKN-74 cells, or the MMC-resistant SK-GT-5 cells, as quantified by both bisbenzimide trihydrochloride staining and the TdT assay (24). In addition, the typical oligonucleosomal base pair fragments (DNA "ladders") were not induced by safingol under the conditions tested. When exposed to MMC alone, apoptosis was induced in both cell lines although to different degrees. However, addition of safingol significantly potentiated this apoptotic response. For MKN-74 cells MMC induced apoptosis in 40% of the cells, whereas the combination of MMC and safingol induced apoptosis in 83% of the exposed cells. With the SK-GT-5 cells, MMC alone induced apoptosis in 18% of the cells, whereas the combination of safingol and MMC induced apoptosis in 39% of the cells (24). These studies showed that safingol potentiated the cytotoxic effect of MMC in two human gastric cancer cell lines which differed in their baseline sensitivity to MMC and in their p53 status. Applicants have observed a similar potentiation of apoptosis by safingol in combination with other chemotherapeutic agents, including doxorubicin, against the gastric cancer cells.

In order to test whether the effect of safingol in inducing apoptosis was due to its anti-PKC effect, applicants performed comparable studies with safingol in the presence of the phorbol ester, 3-phorbol 12-myristate 13-acetate (PMA), which activates PKC by binding to its amino-terminal regulatory domain (25). Safingol, as a sphingosine, inhibits PKC activity by interfering with the function of PKC's regulatory domain (26). Therefore, applicants hypothesized that if the potentiation of MMC-induced apoptosis by safingol is mediated by inhibition of PKC, then PMA should abrogate this effect. In applicants' studies with the gastric cancer cells, PMA effectively abrogated the safingol effect of potentiating MMC-induced apoptosis in this cells, supporting the hypothesis that this process is a PKC-dependent event (22).

Applicants' studies demonstrate that safingol sensitizes gastric cancer cells, with either wild-type or mutated p53, to the induction of apoptosis by MMC. Applicants therefore sought to determine whether this effect by safingol on MMC induced apoptosis could be detected in breast cancer cells.

PRELIMINARY STUDIES

For these studies applicants used MDA-MB-468 breast cancer cells which have a mutation in p53 (7) and have PKC enzyme activity, as determined by enzyme extraction on a DEAE-52 column and assayed for PKC activity by incorporation of [$\gamma^{32}$P]ATP into myelin basic protein. For determination of apoptosis MDA-MB-468 cells were treated according to one of several conditions: (i) no drug (control) for 24 hours, (ii) Safingol alone (50 $\mu$M) for 24 hours. (This concentration represents the highest non-toxic dose of safingol for the MDA-MB-468 cells, as determined by cell proliferation studies, and slightly exceeds the safingol concentration (30 $\mu$M) which inhibits PKC enzyme activity by 50% in vitro.), (iii) Mitomycin-C alone (2.5 $\mu$g/ml) for 24 hours, (iv) Mitomycin-C alone (5 $\mu$g/ml) for 24 hours, (v) the combination of safingol (50 $\mu$M) and Mitomycin-C (2.5 $\mu$g/ml) for 24 hours, (vi) the combination of safingol (50 $\mu$M) and Mitomycin-C (5 $\mu$g/ml) for 24 hours. Apoptosis was measured by quantitative fluorescent microscopy (QFM) of nuclear changes induced by apoptosis, as determined by bisbenzimide trihydrochloride (Hoescht-33258) staining of condensed nuclear chromatin (24). For the QFM duplicate samples of 500 cells each were counted and scored for the incidence of apoptotic chromatin condensation using an Olympus BH-2 fluorescence microscope. The results are shown in FIG. 9. MMC alone at the concentrations of 2.5

μg/ml and 5.0 μg/ml induced apoptosis in 4%±2 and 6%±1 of the MDA-MB-468 cells, respectively. However, the combination of safingol (SPC) and MMC significantly increased the percentage of cells undergoing apoptosis from 11%±1 with safingol alone to 23%±2 with safingol and 2.5 μg/ml MMC and to 33%±10 with safingol and 5.0 μg/ml MMC (p<0.001).

Applicants also tested the PKC inhibitor UCN-01 (27) which is currently in phase I clinical trial at the NCI. In contrast to safingol, which inhibits PKC by binding to its regulatory domain, UCN-01 inhibits PKC at its catalytic domain. Therefore, assessment of the effect of UCN-01 on inducing apoptosis in combination with MMC on MDA-MB-468 was also performed. The QFM method to quantitate apoptosis was again used. The conditions tested were identical to those described above for safingol except UCN-01 (1 μM) was substituted for safingol in all the conditions. The results are shown in FIG. 10. The combination of UCN-01 and MMC together increased the induction of apoptosis of the MDA-MB-468 cells from 20%±4 with UCN-01 alone to 41%±3 with UCN-01 and 2.5 μg/ml MMC and to 58%±1 with UCN-01 and 5.0 μg/ml MMC.

These results indicate that even though the PKC inhibitors safingol and UCN-01 can by themselves induce a slight degree of apoptosis in the breast cancer cells the induction of apoptosis is greatly enhanced when the PKC inhibitors are given in combination with MMC. The demonstration that these agents potentiate chemotherapy induced apoptosis may have important clinical implications in view of the recent introduction of these two agents into clinical trials. Of particular importance is the finding that these agents are effective even with tumor cells that have a mutation in p53. Hence the use of PKC inhibitors may provide a new approach to overcoming drug resistance in tumor cells that are resistant to chemotherapy because they lack p53 function. The purpose of these studies is then to determine how to optimize this effect in breast cancer cells by examining the best combinations of PKC inhibitors with chemotherapy as well as to examine the cellular basis of this phenomenon.

METHODS and PLAN

To determine the optimal chemotherapeutic agent(s) to combine with the PKC specific inhibitor safingol and UCN-01 in the induction of apoptosis. Both Safingol and UCN-01 are now in phase I clinical trials. Combining these agents with chemotherapeutic agents appears to be the best way to maximize the beneficial effects of these drugs as anti-cancer agents against breast cancer cells. However, the optimal chemotherapeutic agent to combine with safingol and UCN-01 against breast cancer cells remains to be defined. The plan is to perform studies with safingol and UCN-01 in combination with other conventional chemotherapeutic agents such as cis-platin, Taxol, 5-fluorouracil and doxorubicin in order to determine the extent to which safingol and UCN-01 induce apoptosis with these other agents. For these studies applicants will use MDA-MB-468 cells. Applicants will also test other breast cancer cell lines, including MCF-7 and MCF-7 sublines resistant to doxorubicin and cisplatin, in order to determine whether this phenomenon of enhancing the induction of apoptosis with PKC inhibitors is more generalized. Apoptosis will be quantitated by two methods: (1) QFM staining: This method involves staining with bisbenzimide trihydrochloride (Hoescht-33258) of condensed chromatin which characterizes the cells undergoing apoptosis (24), and (ii) terminal deoxynucleotidyl transferase (TdT) assay which labels the 3'-OH ends of DNA fragments in apoptotic cells (24,28).

For QFM determinations, the cells are fixed in 3% paraformaldehyde and incubated at room temperature for 10 minutes. The fixative is removed and the cells are washed with 1× PBS, resuspended in 20 μl 1× PBS containing only 8 μg/ml of bisbenzimide trihydrochloride (Hoechst #33258), and incubated at room temperature for 15 minutes. Aliquots of the cells (10 μl) are placed on glass slides coated with 3-amino-propyl-triethoxysilane, and duplicate samples of 500 cells each were counted and scored for the incidence of apoptotic chromatin condensation using an Olympus BH-2 fluorescence microscope equipped with a BH2-DM2U2UV Dich. Mirror Cube filter (Olympus, Lake Success, N.Y.).

For the TdT assays, the ApopTag Kit (Oncor, Gaithersburg, Md.) is used. This method employs a fluoresceinated antidigoxigenin antibody directed against nucleotides of digoxigenin-11-dUTP (d-dUTP) which are catalytically added to the 3-OH ends of fragmented DNA by TdT. Briefly, 1–2×10$^6$ cells were washed and fixed with 1% paraformaldehyde. The fixed cells are incubated in a reaction mixture containing TdT and d-dUTP for 30 minutes at 37° C. Stop/wash buffer is added, and the cells are resuspended in 100 μl of fluorescinated anti-digoxigenin antibody for 30 minutes at room temperature. The cells are then washed with 0.1% Triton X-100 and counterstained with propidium iodide (PI) solution. Green (d-dUTP labeled DNA strand breaks) and red (PI staining for total DNA content) fluorescence of individual cells are measured on a FACScan flow cytometer (Becton Dickinson, San Jose, Calif.). The resulting bivariate plots enables the detection of apoptotic events within the cell cycle. The $R_1$ cursor is set using the control specimen to define normal levels of green fluorescence (i.e., basal levels of apoptosis). Cells with fluorescence above the $R_1$ cursor are considered apoptotic. The data from 10,000 cells are collected and analyzed using CellFit and LYSYS software (Becton Dickinson).

To evaluate other novel PKC inhibitors in combination with chemotherapy to determine their effect on induction of apoptosis. Selective PKC inhibitors other than safingol and UCN-01 may induce even greater degrees of apoptosis when combined with chemotherapy against breast cancer cells. The other PKC inhibitors to be tested for the induction of apoptosis against the breast cancer cells will include RO 32-0432 (29), a specific inhibitor of PKC's catalytic domain (supplied by Roche Pharmaceuticals, Nutley, N.J.), and bryostatin 1 (30), an agent that activates PKC with short exposure but inhibits PKC following prolonged drug exposure by inducing PKC degradation. The methods to quantitate apoptosis will be similar to those described above.

To test the optimal combination and sequence of PKC inhibitors with chemotherapy. Since many of these inhibitors act at different sites of the enzyme (regulatory vs. catalytic), it may be possible to combine multiple PKC inhibitors together with chemotherapy in order to further enhance the induction of apoptosis. For example, applicants plan to determine whether the combination of UCN-01 and safingol with MMC at the conditions described above induce a greater degree of apoptosis than treatment either PKC inhibitor alone and MMC. In addition, the exact sequence and timing of the PKC inhibitor relative to chemotherapy exposure in breast cancer cell remains unknown. For these experiments applicants propose exposing the MDA-MB-468 cells to safingol (50 μM) for different time intervals (30 minutes, 1 hour, 3 hours, 6 hours, 18 hours, and 24 hours), washing the cells free of drug, and then exposing to MMC 5 μg/ml) for 24 hours. The relative induction of apoptosis will then be quantitated as above. Conversely, cells will first be exposed to safingol for 24 hours, but the MMC exposure will now be limited to different time intervals before being assayed for apoptosis.

To determine whether a specific PKC isoform may be a critical target for drug development in inducing apoptosis in breast cancer cells; PKC comprises a multigene family, consisting of at least 13 distinct genes designated α, β, γ, δ, ε, ζ and L (7). The β gene actually yields two distinct transcripts designated $\beta_1$ and $\beta_2$. These isoforms show differential tissue expression, exhibit differences in enenzymatic properties, and may carry out different specialized functions. Their role in apoptosis remains unknown. Since PKC is expressed to some degree in even normal breast tissue (14), it would be ideal to identify PKC isoforms that are unique to human breast tumors. Identifying such an isoform and directly relating the expression of this isoform to the induction of apoptosis in breast cancer cells would provide a strong rationale for drug development of isoform specific inhibitors in this disease. Already some progress has been made in this area with the development of antisense oligonucleotides. A 20 mer has been developed that specifically inhibits the expression of human PKCα without affecting the expression of other PKC isoforms (31). It has also been shown, as a single agent, to inhibit growth of subcutaneously implanted human tumor xenografts. Recent data has, in fact, implicated PKCα in apoptosis of bovine aortic endothelial cells. These studies indicate that only if PKCα is inhibited (e.g defined in these studies as inability to translocate from the cytosol to the active membrane fraction) can apoptosis proceed (22).

In order to pursue this further in breast cancer cells, applicants first propose identifying those isoforms that are expressed in the MDA-MB-468 cells and determining whether the PKC inhibitors (i.e safingol and UCN-01) affect their protein expression in the presence or absence of MMC. Since the distribution of the PKC isoforms between the cytosolic and membrane fraction of the cells appears to be the critical event for their relative activation, applicants will obtain cytosolic and membrane fractions, as described (13), to determine whether there are differences in isoform expression and localization with the different drug treatments that applicants have shown induce apoptosis.

Briefly, PKC will be extracted from the breast cancer cells, using a 20 mM Tris-HCl (pH 7.5) buffer containing 2 mM EDTA, 2 mM EGTA, 5 mM β-mercaptoethanol, 0.5 mM phenylmethylsulphonyl fluoride, 10 ug/ml leupeptin, and 0.25M sucrose (Buffer A). Briefly cells will be homogenized with a 80 strokes (the minimum number required to break the breast cancer cells) of a hand-held Dounce homogenizer. The cell homogenates will then be centrifuged at 100,000×g for 1 hour at 40° C. The supernatant represents the cytosolic fraction and the pellet which is resolubilized in buffer A containing 0.1% Triton-X represents the membrane fraction. These fractions are then passed through a DEAE-52 column and the PKC protein is eluted off the column with Buffer A containing 0.15M NaCl. Briefly, cells are lysed following drug treatment with lysis buffers containing protease and phosphatase inhibitors. Proteins are resolved by SDS-PAGE electrophoresis. Immunoblots are prepared with Immobilon P membranes by electrophoretic transfer and blocked in TN-Tween buffer (50 mM Tris, pH 7.5, 200 mM NaCl, 0.1% Tween-20) containing 5% (w/v) nonfat dry milk. After washing the blots are incubated with horseradish peroxidase-conjugated secondary antibodies (dilution 1/2000. Immunologically reactive protein will be visualized with the enhanced chemiluminescence system (Amersham, Arlington Heights, Ill.). using PKC isoform specific antibodies (Santa Cruz Biotechnology, Inc. Santa Cruz, Calif.).

To assess the relationship between PKC and the cell cycle: The results with gastric cancer cells indicate that p53 is not critical to the induction of apoptosis with PKC inhibition since this phenomenon is observed in the presence of tumor cells with wild type and mutant p53. The preliminary studies with the breast cancer cell line MDA-MB-468, which is known to contain a mutation in p53, would support this hypothesis and would indicate that the effect of PKC inhibitors on enhancing MMC-induced apoptosis is independent of the p53 status of the cells. The existence of a p53-independent pathway for growth arrest has been reported (32). Further studies to define the effects of safingol, especially as it pertains to PKC and steps independent of p53 in the cell cycle of breast cancer cells are proposed. Preliminary data from applicants' lab would indicate that the critical event for induction of apoptosis by PKC inhibition takes place at the G1/S interphase. Proteins implicated in regulating this phase of the cell cycle are the cyclin kinases, including cyclin dependent kinase 2, and the cyclin kinase inhibitors, including p21 and p27. In order to magnify the effect of treatment on these events in the cell cycle, the MDA-MB-468 cells will be synchronized with nocadozole (0.2 μg/ml) for 18 hours, washed thoroughly for 4 hours, and then exposed to 50 μM safingol for 24 hours in the presence or absence of MMC (5 μg/ml). Control cells will be treated in the same way as described above except that standard media without drug will be used for all incubations.

The plan is to examine the effect of safingol and chemotherapy (i.e MMC) on the expression and activation of these proteins by: 1) protein expression with immunoblotting using an enhanced chemiluminescence system; 2) differences in protein phosphorylation with [$^{32}$P]orthophosphate cell labelling, as previously described (33); 3) and cyclin dependent kinase activity as measured by the histone H1 kinase assays (34).

The protein kinase C(PKC) inhibitors UCN-01 and flavopiridol (Flavo) significantly enhance the cytotoxic effect of chemotherapy by promoting apoptosis in gastric and breast cancer cells.

We have reported that the PKC inhibitor safingol significantly enhances the cytotoxic effects of Mitomycin-C (MMC) by promoting MMC-induced apoptosis in gastric cancer cells (*JNCI* 87: 1394, 1995). Both UCN-01 and Flavo inhibit PKC. These drugs are cytotoxic to tumor cells and have been reported to induce apoptosis. Our studies with safingol indicate that the effectiveness of UCN-01 and Flavo on inducing apoptosis would be greatly enhanced by combining them with chemotherapy. In order to test this hypothesis we elected to treat gastric cancer cells, MKN-74 and SK-GT-2, as well as breast cancer cells, MDA-MB-468, with UCN-01 (7.5 to 10 μM) or Flavo (300 nM) in the presence or absence of MMC (5 μg/ml) or Taxol (50 μM) for 24 hours. Induction of apoptosis was estimated by counting the frequency of condensed nuclear chromatin with Hoechst-33258 stain in duplicate samples of 400 cells. The results are summarized as follows:

| Cell Line | No drug | MMC | Flavo | Flavo + MMC |
|---|---|---|---|---|
| MKN-74 | 1% ± 1 | 7% ± 1 | 17% ± 2 | 73% ± 1, p<.001 |

| Cell Line | No drug | Taxol | UCN-01 | UCN-01 + Taxol |
|---|---|---|---|---|
| MKN-74 | 1% ± 1 | 2% ± 1 | 10% ± 2 | 28% ± 9, p<.05 |

| Cell Line | No drug | MMC | UCN-01 | UCN-01 + MMC |
|---|---|---|---|---|
| SK-GT-2 | 1% ± 1 | 11% ± 2 | 18% ± 4 | 53% ± 1, p<.001 |
| MDA-MB-468 | 1% ± 1 | 6% ± 1 | 20% ± 1 | 58% ± 1, p<.001 |

These results indicate that even though both UCN-01 and Flavo can induce apoptosis as single agents their greatest effect is observed when they are combined with chemotherapy. These studies suggest that combinations of these agents with classical chemotherapeutic drugs may improve the efficacy of chemotherapy in both gastric and breast cancer.

References of the Third Series of Experiments

1. Wingo P. A., Tong T., and Bolden S. Cancer Statistics, 1995. CA 45:19–36,1995.
2. Hortobagyi G. N., and Buzdar A. U. Current status of adjuvant systemic therapy for primary breast cancer: progress and controversy. CA 45: 199–226.
3. Schwartz G. K., and Bhardwaj S. Chemotherapy of breast cancer In: Gunter Deppe (ed.): Chemotherapy of gynecologic cancer, second edition: 303–362, 1990.
4. Goldstein L. J., Galski H., Fojo A., Willingham M., Lai S.-L., Gazdar A., et al. Expression of a multidrug resistance in human cancers. J. Natl. Cancer Inst. 81:116–24, 1989.
5. Lowe S. W., Ruley H. E., Jack T., Housman D. E. p53-Dependent apoptosis modulates the cytotoxicity of anticancer agents. Cell 74: 957–967, 1993.
6. Koechii O, Schaer G. N., Seifert B., Hornung R., Haller U., Eppenberger U., Mueller H. Mutant p53 protein associated with chemosensitivity in breast cancer specimens. Lancet 344: 1647–1648, 1994.
7. Thor A. D., Moore D. H., Edgerton S. M., Kawasaki E. S., Reihsaus E., Lynch H. T. et al. Accumulation of p53 tumor suppressor gene protein: an independent marker of prognosis in breast cancers. J. Natl. Cancer Institute 84: 845–55, 1992.
8. Davidoff A. M., Kerns B. J., Pence J. C., Marks J. R., and Iglehart J. D. p53 alterations in all stages of breast cancer. J. Surg. Oncol. 48: 260–267, 1991.
9. Nishizuka Y. The role of PKC in cell surface signal transduction and tumor promotion Nature, 308: 693–698, 1984.
10. Housey G. M., Johnson M. D., Hsiao W. L. W., O'Brian C. A., Murphy J. P., Kirschmeirer P., and Weinstein I. B. Overproduction of protein kinase C causes disordered growth control in rat fibroblasts. Cell 52: 343–354, 1988.
11. Schwartz, G. K., Redwood S. M., Ohnuma T., Holland J. F., Droller M. J., and Liu B. C. S. Inhibition of invasion of invasive human bladder carcinoma cells by protein kinase C inhibitor staurosporine. J. Natl. Cancer Inst. 82: 1753–1756, 1990.
12. Schwartz G. K., Jiang J., Kelsen D. P. and Albino A. P. Protein kinase C: a novel target for inhibiting gastric cancer cell invasion. J. Natl. Cancer Inst., 85: 402–407, 1993.
13. Schwartz G. K., Arkin H., Holland J. F. and Ohnuma T. Decreased protein kinase C activity and multidrug resistance in MOLT-3 human lymphoblastic leukemia cells resistant to trimetrexate. Cancer Res., 51: 55–61, 1991.
14. O'Brian C., Vogel V. G., Singletary S. E., and Ward N. E. Elevated protein kinase C expression in human breast tumor biopsies relative to normal breast tissue. Cancer Res. 49: 3215–3217, 1989.
15. Adams L. M., Dykes D., Harrison S. D., Saleh J., and Saah L. Combined effect of the chemopotentiator SPC-100270, a protein kinase C inhibitor, and doxorubicin or cisplatin (Cis) on murine isografts and human tumor xenografts. Proc. Amer. Assoc. Cancer Res. 34:410, 1993.
16. Schwartz G. K., Ward D., Saltz L. Casper E., et al. A phase I study of the protein kinase C specific inhibitor safingol alone and in combination with doxorubicin. Proc. Amer. Soc. Clin. Onc. 14:1557,1995.
17. Sachs C. W., Safa A., and Fine R. L. Inhibition of protein kinase C by Safingol is associated with chemosensitization of multidrug resistant MCF-7 cells. Proc. Amer. Assoc. Cancer Res. 35:447, 1994.
18. Adams L. M., Cofield D. J., Seldin J. C., Kitchen P. A., et al. Effect of the protein kinase C (PKC) inhibitor SPC-100270 on drug accumulation and cytotoxicity in drug resistant and sensitive tumor cell in vitro. Proc. AACR 34:410, 1993.
19. Evans D. L. and Dive C. Effects of cisplatin on the induction of apoptosis in proliferating hepatoma cells and nonproliferating immature thymocytes. Cancer Res. 53: 2133–2139, 1993.
20. Jarvis W. D., Turner A. J., Povirk L. F., Traylor R. S., and Grant S. Induction of apoptotic DNA fragmentation and cell death in HL-60 human promyelocytic leukemia cells has been reported for pharmacological inhibitors of protein kinase C. Cancer Res. 54: 1707–1714, 1994.
21. McConkey D. J., Hartzell P., Jondal M., and Arrenius S. Inhibition of DNA fragmentation in thymocytes and isolated thymocyte nuclei by agents that stimulate protein kinase. J. Biol. Chem. 264: 13399–13402, 1989.
22. Haimovitz-Friedman A., Balaban N. A., McLoughlin M., Ehleiter D., Michaeli J., Vlodavsky I., and Fuks Z. PKC mediates basic fibroblast growth factor of endothelial cells against radiation-induced apoptosis. Cancer Res. 54: 2591–2597,1994.
23. Nabeya Y., Loganzo F., Maslak P., Lai L., de Oliveira A., Schwartz G. K. et al. The mutational status of p53 protein in gastric and esophageal adenocarcinoma cell lines predicts sensitivity to chemotherapeutic agents. Int. J. Cancer 64: 1–10, 1995.
24. Schwartz G. K., Haimovitz-Friedman A., Dhupar S. K., Ehleiter D., Maslak P., Loganzo F., Kelsen D. P., Fuks Z., Albino A. P. Potentiation of apoptosis by treatment with the protein kinase C specific inhibitor safingol in mitomycin-c treated gastric cancer cells. J. Natl. Cancer Institute 87(18): in press, 1995.
25. Hannun Y. A., Loomis C. R., Merrill A. H., and Bell R. M. Sphingosine inhibition of protein kinase C activity and of phorbol dibutyrate binding in vitro and in human platelets. J. Biol. Chem. 261: 12602–12609, 1986.
26. Blumberg P. M. Protein kinase C as the receptor for the phorbol ester tumor promoter: Sixth Rhoads memorial award lecture. Cancer Res. 48: 1–8, 1988.
27. Takahashi I., Saitoh Y., Yoshida M., Sano H., et al. UCN-01 and UCN-02, new selective inhibitors of protein kinase C. J. Antibiot. 42: 571–576, 1989.
28. Schmitz G., Walter T., Serbel R., and Kessle C. Nonradioactive labeling of oligonucleotides in vitro with the hapten digoxigenin by tailing with terminal transferase. Anal. Biochem. 192: 222–231, 1991.

29. Birchall A. M., Bishop J., Bradshaw D., Cline A., Coffey J., Elliott L. H., et al. RO 32-0432, a selective and orally active inhibitor of protein kinase C prevents T-cell activation. *J. Pharmacol. Exp. Therapeutics*, in press, 1995.
30. Kraft A. S., Smith J. B., and Berkow R. L. Bryostatin, an activator of calcium phospholipid-dependent protein kinase, blocks phorbol ester-induced differentiation of human promyelocytic HL-60 cells. *Proc. Natl. Acad. Sci. USA* 83:1334–1338,1986.
31. Dean N. M., McKay R., Miraglia L., Marcel M., Fabbro D. Inhibition of growth of xenografted human tumor cell lines in the nude mice by an antisense oligonucleotide targeting human PKCα. *Proc. Amer. Assoc. Cancer Res.* 36: 413, 1995.
32. Johnson M., Dimitrov D., Vojta P. J., Barrett J. C., Noda A., Pereira-Smith O, and Smith J. Evidence for a p53-independent pathway for upregulation of SDI1/CIP1/WAF1/p21 RNA in human cells. *Mol. Carcinogenesis* 11: 59–64, 1994.
32. Xiong Y., Zhang H., and Beach D type cyclins associate with multiple protein kinases and DNA replication and repair factor. *Cell* 71: 505–514, 1992.
34. Koff A., Cross F., Fisher A., Schumacher J., Leguelle K., Philippe M., and Roberts J. Human cyclin E, a new cyclin that interacts with two members of the cdc2 gene family. *Cell* 66: 1217–1228, 1991.

Fourth Series of Experiments

To evaluate the ability of the PKC inhibitor RO 32-2241 to increase the sensitivity of gastric cancer cells to the cytotoxic effects of Mitomycin-C.

Gastric cancer is one of the leading causes of cancer death throughout the world. The reported 5 years survival of surgically resected patients approaches 15–20% while the overall survival of patients with gastric carcinoma is approximately 10%. Currently there are no effective regimens for inhibiting the growth gastric cancer. Therefore, the identification of an agent which inhibits the growth of gastric cancer may have a significant clinical impact on prolonging the survival of patients with this disease.

A large body of evidence indicates a fundamental role for the involvement of protein kinase C (PKC), a family ofserine/threonine protein kinases, in processes related to neoplastic transformation, carcinogenesis, and tumor cell invasion. Consequently, PKC may present a novel target for anti-cancer therapy. RO 32-2241, is a bisindolymaleimide that inhibits PKC by binding to its catalytic site. Introduction of a cationic side chain and conformational restriction of the amine side chain has resulted in an agent that is highly selective for PKC and which can penetrate cells. Preclinical animal studies show that RO 32-2241 is non-toxic at doses that achieve serum levels sufficient to inhibit PKC-driven responses. For example, this agent has been shown to be an inhibitor of T cell activation and phorbol ester induced paw edema in female AHH/R rats. However, despite extensive evaluation of this agent as an anti inflammatory drug, there has been no formal testing of this agent in cancer therapy.

It has been shown that PKC activity can act as an antagonist to apoptosis, whereas PKC inhibition can promote apoptosis. These observations imply that one function of PKC stimulated processes is to inhibit the induction of programmed cell death. Thus, anti-tumor effects of chemotherapeutic agents may be potentiated by PKC inhibitors that contribute to the induction of apoptosis after drug-induced damage. In order to test this hypothesis we have used the human gastric cancer cell MKN-74 to determine whether RO 32-2241 would enhance the cytotoxic effect of the chemotherapeutic agent Mitomycin-C (MMC). Cytotoxicity was measured and quantified using the Alamar Blue Assay. Cells were treated according to one of four conditions: (i) no drug (control) for 24 hours, (ii) RO 32-2241 alone at 10–6M, (iii) Mitomycin-C alone at 5 µg/ml for 24 hours, (iv)the combination of RO 32-2241 (10–6M) and Mitomycin-C (5µg/ml) for 24 hours. The results are summarized below for percent survival:

| Drug Treatment | Percent survival |
| --- | --- |
| MMC | 87% |
| RO 32-2241 alone | 100% |
| Combination of MMC + RO 32-2241 | 42% |

Thus, treatment of these cells with either RO 32-2241 or MMC alone had essentially minimal or no effect on inhibiting cellular proliferation;whereas the combination of these two agent at the same concentrations was exceptionally toxic to the MKN-74 cells.

In contrast to safingol, the PKC inhibitor currently in clinical at MSKCC, RO 32-2241 is a more protent and selective inhibitor of PKC. Whereas safingol inhibits PKC in micromolar ranges, RO 32-2241 inhibits PKC activity in nanomolar ranges. Therefore, in view of its exceptionally potency and specificity there are theoretical advantages for the development of RO 32-2241 for clinical trial. The purpose of the present study therefore is to determine whether effect that we are observing with RO 32-2241 in combination with mitomycin-C in vitro can also be achieved in tumor bearing animals in vivo.

The PKC inhibitor for these studies will be RO 32-2241. The dose and schedule of the PKC inhibitor for this study (30 mg/kg), i.p./day, ×4 weeks) is based on preclinical toxicology, which has been generated by ROCHE Research center (Welwyn Garden City, UK). The dose appears to be a safe and well-tolerated dose when administered i.p. to MF1 mice. It has been shown to effectively inhibit PKC-mediated responses (e.g paw edema) in animals. This effect has been shown to persist for up to 6 hours when Ro 32-2241 is administered either 1 or 24 hours before challenge with an inflammatory stimulus. The inhibitor will be formulated by sonicating in 10% succinylated gelatin to form a solution appropriate for i.p. injection. This will be freshly prepared every 5 days. (The 10% succinylated gelatin is prepared by slowly dissolving in distilled water, stirring continuously, and heated below 60° C. One prepared it is autoclaved and stored below 5° C.) Doses of 200 mg/kg/day have been given to mice on this schedule with no major animal toxicity or deaths.

The decision to combine RO 32-2241 with MMC is based on our pre-clinical data which indicated that RO 32-2241 enhanced the cytotoxicity of MMC. The dose of MMC selected for these studies will be 4 mg/kg in saline. The dose has been safely administered to nude mice and has also been safely administered to nude mice when combined with the PKC inhibitor UCN-01 (Akinaga et al., Enhancement of anti-tumor activity of mitomycin C in vitro and in vivo by UCN-01, a selective inhibitor of protein kinase C. *Cancer Chem Pharm* 32: 183–189, 1993).

The protocol design will be as follows: All animals with be injected subcutaneously into the hind quarter on day 1 with $5 \times 10^6$ MKN-74 cells. Our preclinical data indicates that within 10–12 days these animals develop a palpable 0.25 gr. tumor mass. Once the animals have a palpable tumor, they will be randomly assigned to one of 4 treatment arms (17 animals in each arm) on day #1:

1) Ro 32-2241: by itself at a dose of 30 mg/kg/day i.p. starting day #1 for 4 weeks.

2) MMC alone: administered alone (4.0 mg/kg) i.v., x1, day #1.
3) RO 32-2241+MMC: Ro32-2241 will be given at a dose of 30 mg/kg/day i.p. starting day #1 and repeated daily for 4 weeks. One hour following the day #1 i.p. injection of RO 32-2241, MMC will be given as a single i.v. dose (4.0 mg/kg)

| Group (17 animals/ group) | RO 32-2241 (30 mg/kg/day, i.p., × 4 weeks) | Mitomycin-C (4.0 mg/kg, × 1, day #1) | Saline controls |
|---|---|---|---|
| I | + | − | − |
| II | − | + | − |
| III | + | + | − |
| IV (control) | − | − | + |

Following the final dose of RO 32-2241 each treatment arm will be divided into 3 groups (5 animals/subgroup) and each subgroup will then be used for 0 hr, 1 hr, and 3 (or 6) hour time points for blood collection following the final dose of RO 32-2241. Blood samples will be collected into EDTA tubes.

Plasma will be separated by centrifugation (2000 g; 10 min, at 4° C., if possible) within 2 hours of collection and stored at −20° C.

Fifth Series of Experiments

Evaluation of the Protein Kinase C α Anti-sense, Both by Itself and in Combination with Mitomycin-C, as a New Anti-Cancer Treatment for Gastric Cancer To evaluate the anti-tumor activity of the PKC α anti-sense both by itself and in combination with mitomycin-C against gastric cancer.

A large body of evidence indicates a fundamental role for the involvement of protein kinase C (PKC), a family of serine/threonine protein kinases, in processes related to neoplastic transformation, carcinogenesis, and tumor cell invasion. Consequently, PKC may present a novel target for anti-cancer therapy. It has been shown that PKC activity can act as an antagonist to apoptosis, whereas PKC inhibition can promote apoptosis. These observations imply that one function of PKC stimulated processes is to inhibit the induction of programmed cell death. Thus, anti-tumor effects of chemotherapeutic agents may be potentiated by PKC inhibitors that contribute to the induction of apoptosis after drug-induced damage.

In order to test this hypothesis applicants have used gastric cancer cells (MKN-74 and SK-GT-5) to determine the induction of apoptosis with the PKC inhibitor safingol alone and in combination with the chemotherapeutic agent Mitomycin-C. Safingol is ideal for these experiments since it specifically inhibits PKC activity by binding to the enzymes's regulatory domain, a site which is unique to PKC. This is in contrast to other PKC inhibitors such as staurosporine which inhibit PKC enzyme activity by binding to the enzyme's catalytic domain, a site that is highly homologous to the catalytic domain of other protein kinases.

For these studies apoptosis was measured by quantitative fluorescent microscopy (QFM) determination with bisbenzimide trihydrochloride stain (Hoescht-33258) for condensed nuclear chromatin characteristic of apoptotic cells. Gastric cancer cells (MKN-74) were treated according to one of several conditions: (i) no drug (control) for 24 hours, (ii) safingol alone at 50 μM, the highest non-toxic dose as determined by cell proliferation studies with [$^3$H]-thymidine for 24 hours; (iii) Mitomycin-C alone (5 μg/ml) for 24 hours; (iv) the combination of safingol (50 μM) and Mitomycin-C (5 μg/ml) for 24 hours. The doses of MMC used was based on cell proliferation studies with [$^3$H]-thymidine with gastric cancer cells that indicate<20% inhibition of proliferation.

For QFM determinations 500 cells were counted and scored for the incidence of apoptotic chromatin changes under an Olympus BH-2 fluorescence microscope in duplicate samples, ±SD, using a BH2-DM2U2UV Dich. Mirror Cube filter. The results were summarized in FIG. 2.

As the results indicate treatment of MKN-74 cells with safingol alone did not induce apoptosis in these cells. However, the combination of safingol with Mitomycin-C induced an increase in apoptosis in a dose-dependent fashion when compared to treatment with Mitomycin-C alone. The percentage of cells undergoing apoptosis increased from 40% with Mitomycin-C alone to 80% with the combination therapy. This effect was observed in cells with wild type (MKN-74) or mutated (SK-GT-5) p53 indicating that this effect was independent of the p53 status of the cells (Schwartz GK, et al, Potentiation of apoptosis by treatment with the protein kinase C specific inhibitor safingol in Mitomycin-C treated gastric cancer cells, JNCI, In press). Applicants have obtained similar results with other human gastric cancer cell line that including SK-GT-1, SK-GT-4, SK-GT-5. Each of these cell lines has a mutation in p53 and exhibits drug resistance to chemotherapy (including MMC). Thus, PKC inhibitors appear to represent a novel way to enhance chemotherapy sensitivity even in tumor cells that are resistant to chemotherapy by virtue of their p53 mutational status.

These results indicate that PKC represents a novel target for enhancing the induction of apoptosis when combined with chemotherapy. However, PKC is ubiquitous in both normal and malignant tissue. Even though safingol represents a considerable advance in the development of PKC inhibitors especially as they pertain to eventual clinical development, further specificity would still provide theoretical advantages in drug development. PKC exists as a multi-gene family with multiple isoforms that are both tumor and site specific. The role of these different isoforms is essentially unknown. However, identifying the isoform(s) involved in apoptosis would provide a more specific target for drug therapy. Recent data have implicated PKCα in apoptosis. Studies have shown that if PKCα is inactivated then apoptosis can proceed (Haimovitz-Friedman et al, Protein kinase C mediates basic fibroblast growth factor protection of endothelial cells against radiation-induced apoptosis, *Cancer Res.* 54: 2591–2597, 1994).

Most attempts to develop PKC isoform specific inhibitors have been unsuccessful. However, some inroads have been made with PKCα by testing of antisense oligonucleotides. A 20 mer has been developed by Isis Pharmaceuticals (Carlsbad, Calif. 92008) which specificly inhibits the expression of human PKCα without affecting the expression of other PKC isoforms. It has been shown to inhibit the growth of subcutaneously implanted human tumor xenografts. This inhibition was dose-dependent when administered intravenously (i.v.) or intraperitoneally (i.p.) between 0.06 and 6 mg/ml (Dean, N. et al. Inhibition of growth of xenografted human tumor cell lines in nude mice by an antisense oligonucleotide targeting human PKCα. *Proc. AACR* 36: 2460, 1995.)

Applicants' results would indicate that the best way to maximize the therapeutic benefits of PKC inhibitors is to combine them with chemotherapy. Applicants have previously reported that all the SK-GT cell lines express PKCα mRNA and protein (Schwartz G. K., et al. Defining the invasive phenotype of proximal gastric cancer cells. *Cancer* 73: 22–27, 1994). Therefore, these cell lines appear to be appropriate for the evaluation of a PKCα anti-sense. Applicants' published results on the effect of combining Mitomycin-C with PKC inhibitors is based on in vitro systems. Ultimately, applicants' observation needs to be verified in an in vivo model. Therefore, the goal of this study is to test the combination of the PKCα anti-sense in combination with MMC for the first time in an in vivo system.

Gastric cancer is one of the leading causes of cancer death throughout the world. The reported 5 years survival of surgically resected patients approaches 15–20% while the overall survival of patients with gastric carcinoma is approximately 10%. Currently there are no effective regimens for inhibiting the growth of gastric cancer. Therefore, the identification of an agent which inhibits the growth of gastric cancer may have a significant clinical impact on prolonging the survival of patients with this disease.

The PKC inhibitor for these studies will be a 20 mer PKCα antisense. The dose and schedule of the anti-sense for this study (10 mg/kg, daily, i.p.) will be based on preclinical toxicology, which has been generated by ISIS pharmaceutical. The dose of appears to be a safe and well-tolerated dose when administered both i.p. or i.v. to tumor bearing nude mice. The anti-sense easily dissolves in saline. Doses of 100 mg/kg have been given to mice on a daily schedule with no major toxicity and no deaths. At the highest non-toxic dose (100 mg/kg) mild lymphocytic infiltration has been noted in the liver, spleen and kidney.

In order to determine the specificity of this response, a missense 20 mer will also be administered to two of the control groups. This will ensure that the observed response is secondary to the effect of the PKCα anti-sense and not due to a non-specific effect of the anti-sense therapy. The missense selected has also been safely administered at 10 mg/kg i.p to mice on a daily schedule without significant toxicity.

The decision to combine PKCα antisense with MMC is based on applicants' pre-clinical data which indicated that PKC inhibitors enhanced the induction of MMC-induced apoptosis. The dose of MMC selected for these studies will be 14.5 mg/kg in saline. This dose has been safely administered to nude mice and has also been safely administered to nude mice when combined with the PKC inhibitor UCN-01 (Akinaga et al., Enhancement of anti-tumor activity of mitomycin C in vitro and in vivo by UCN-01, a selective inhibitor of protein kinase C, *Cancer Chem Pharm* 32: 183–189, 1993).

The protocol design will be as follows: All animals with be injected subcutaneously into the hind quarter on day 1 with $5 \times 10^6$ SK-GT-2 cells. Applicants' preclinical; data indicates that within 10–12 days these animals develop a palpable 0.25 gr. tumor mass. Once the animals have a palpable tumor, they will be randomly assigned to one of 4 treatment arms (17 animals in each arm):

1) PKCα anti-sense: by itself at a dose of 10 mg/kg/day i.p. daily for four weeks,
2) PKCα anti-sense+MMC: PKC anti-sense will be given at a dose of 10 mg/kg i.p daily for two weeks. On the first day of week #3 MMC will be given as a single i.v. dose (14.5 mg/kg). PKC anti-sense will be repeated i.p daily for an additional two weeks (i.e. weeks #3 and 4).
3) MMC alone: Daily i.p injections of a saline control for two weeks. On the first day of week #3 a single dose of Mitomycin-C well be administered (14.5 mg/kg) i.v.. This will be followed by two additional weeks of i.p. saline control.
4) PKCα missense: by itself at a dose of 10 mg/kg/day i.p. daily for four weeks.

Because of the nature of anti-sense therapy, in vitro studies are not predictive of in vivo results. For this reason applicants plan to go directly to these animal studies.

Athymic nu/nu mice are ideal recipients of human tumor cells because they will not usually show host versus graft reactions and thus immunologically attack the injected tumor cells.

| Group (17 animals/ group) | PKCα antisense (10 mg/kg I.P, daily, × 28 days) | Mitomycin-C (14.5 mg/kg, day #14) | PKC missense (10 mg/kg i.p, daily, × 28 days) |
| --- | --- | --- | --- |
| I | + | − | − |
| II | − | − | − |
| III | + | + | − |
| IV (control) | − | + | + |

Assuming a "non-treatment" response rate of 5% (i.e. antisense alone or Mitomycin-C alone) relative to the control animals (missense alone), then in order to detect a 50% decrease in size of the palpable tumor mass for the treated group (i.e antisense+Mitomycin-C) using a one sided alternative normal approximation z-test with a significance of 0.05 and a power of 80%, the total number of animals for each group needs to be 17. The total number of animals will be 64.

Sixth Series of Experiments

Structural modification of protein kinase C specific inhibitors predicts for enhancement of mitomycin-C induced apoptosis in gastric cancer cells Applicants have reported that the protein kinase C (PKC) specific inhibitor safingol enhances mitomycin-C (MMC)-induced apoptosis in gastric cancer cells (*JNCI* 87:1394, 1995). To study this further applicants elected to examine five bis-indolylmaleimides with various potencies against PKC. Unlike safingol, which inhibits PKC at its regulatory domain, these compounds inhibit PKC by competing with ATP at its catalytic domain. MKN-74 gastric cancer cells were treated for 24 hours according to one of four conditions: 1) No drug, 2) PKC inhibitor (1 to 4 $\mu$M), 3) MMC alone (5 $\mu$g/ml, 4) MMC+PKC inhibitor. The induction of apoptosis was estimated by counting the frequency of condensed nuclear chromatin with Hoechst-33258 stain in duplicate samples of 400 cells. None of the PKC inhibitors induced a significant degree of apoptosis when given alone. However, only two compounds (RO-A and RO-B) enhanced MMC-induced apoptosis from 10%±2% with MMC alone to 41%±1% with the combination of RO-A and MMC (p<0.001) and to 34%±2% with the combination of RO-B and MMC (p<0.001). Interestingly, other compounds, one with similar potency against PKC (RO-C), did not potentiate MMC-induced apoptosis. Therefore, potent activity against PKC appears to be necessary, but not sufficient, to cause apoptosis in combination with MMC. Examination of the structure of the two active PKC inhibitors indicates a common modification of the indole ring which the other PKC inhibitors lack. These results suggest that this specific modification of bisindolylmaleimides, which confers PKC specificity, has the potential to enhance chemotherapy-induced apoptosis.

What is claimed is:

1. A method for screening for protein kinase C inhibitors which increase induction of apoptosis in tumors cells comprising the steps of:
   (a) contacting tumor cells with an amount of a protein kinase C inhibitor effective to increase induction of apoptosis of the tumor cells;

(b) contacting the tumor cells of step (a) with an antitumor therapeutic agent;

(c) determining the apoptosis of the tumor cells of step (b); and (d) comparing the apoptosis determined in step (c) with the apoptosis of control tumor cells which are only treated with the antitumor therapeutic agent, a greater degree of apoptosis determined in the tumor cells in step (c) than in the control tumor cells indicating that the protein kinase C inhibitor increases induction of apoptosis in those tumor cells.

2. A method for screening for protein kinase C inhibitors which increase induction of apoptosis in tumors cells comprising the steps of:

(a) contacting tumor cells with an amount of a protein kinase C inhibitor in the presence of an antitumor therapeutic agent effective to increase induction of apoptosis of the tumor cells;

(b) determining the apoptosis of the tumor cells of step (a); and (c) comparing the apoptosis determined in step (b) with the apoptosis of control tumor cells which are only treated with the antitumor therapeutic agent, a greater degree of apoptosis determined in the tumor cells in step (b) than in the control tumor cells indicating that the protein kinase C inhibitor increases induction of apoptosis in those tumor cells.

3. A method according to claim 1 or 2, wherein the protein kinase C inhibitor is selected from the group consisting of protein kinase C inhibitors and antisense nucleotides capable of inhibiting the expression of protein kinase C.

* * * * *